(12) United States Patent
Kim et al.

(10) Patent No.: US 10,584,327 B2
(45) Date of Patent: Mar. 10, 2020

(54) ENRICHMENT OF SMALL NUCLEIC ACIDS

(71) Applicant: ABBOTT MOLECULAR INC., Des Plaines, IL (US)

(72) Inventors: Dae Hyun Kim, Des Plaines, IL (US); Gerard J. Gundling, Des Plaines, IL (US); Herbert A. Marble, Des Plaines, IL (US); Mark W. Eshoo, Des Plaines, IL (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 0 days.

(21) Appl. No.: 16/299,326

(22) Filed: Mar. 12, 2019

(65) Prior Publication Data

US 2019/0203197 A1    Jul. 4, 2019

Related U.S. Application Data

(60) Division of application No. 15/728,199, filed on Oct. 9, 2017, now Pat. No. 10,260,063, which is a continuation of application No. 14/921,751, filed on Oct. 23, 2015, now Pat. No. 9,783,799.

(60) Provisional application No. 62/068,443, filed on Oct. 24, 2014.

(51) Int. Cl.
*G01N 1/00* (2006.01)
*G01N 1/18* (2006.01)
*C12N 15/10* (2006.01)

(52) U.S. Cl.
CPC ....... *C12N 15/101* (2013.01); *C12N 15/1003* (2013.01); *C12N 15/1006* (2013.01); *C12N 15/1013* (2013.01); *C12N 15/1017* (2013.01)

(58) Field of Classification Search
CPC .................................. G01N 1/00; G01N 1/18
USPC ................................... 436/43, 174, 175, 177
See application file for complete search history.

(56) References Cited

U.S. PATENT DOCUMENTS

| | | | |
|---|---|---|---|
| 5,652,141 | A | 7/1997 | Henco et al. |
| 5,945,525 | A | 8/1999 | Uematsu et al. |
| 6,020,186 | A | 2/2000 | Henco et al. |
| 6,037,465 | A | 3/2000 | Hillebrand et al. |
| 9,206,469 | B2 | 12/2015 | Forman et al. |
| 10,260,063 | B2 * | 4/2019 | Kim .................... C12N 15/101 |
| 2002/0007054 | A1 | 1/2002 | Sakurai et al. |
| 2003/0215818 | A1 | 11/2003 | Lorenz |
| 2005/0112658 | A1 | 5/2005 | Makino |

(Continued)

FOREIGN PATENT DOCUMENTS

WO   WO 2007140417 A2   12/2007
WO   WO 2010115016 A2   10/2010

(Continued)

OTHER PUBLICATIONS

Bettegowda C., et al., "Detection of Circulating Tumor DNA in Early-and Late-Stage Human Malignancies," Science Translational Medicine, 2014, vol. 6 (224), p. 224ra24.

(Continued)

*Primary Examiner* — Brian J. Sines
(74) *Attorney, Agent, or Firm* — Casimir Jones, S.C.; Kirk Hogan

(57) ABSTRACT

Provided herein is technology related to processing samples of nucleic acids and particularly, but not exclusively, to methods for enriching samples for small nucleic acids, such as small circulating cell-free DNA.

22 Claims, 8 Drawing Sheets

(56) References Cited

U.S. PATENT DOCUMENTS

| | | |
|---|---|---|
| 2009/0081802 A1 | 3/2009 | Ritt |
| 2010/0105049 A1 | 4/2010 | Enrich et al. |
| 2011/0257382 A1 | 10/2011 | Willson et al. |
| 2012/0083597 A1 | 4/2012 | Okamoto et al. |
| 2012/0178918 A1 | 7/2012 | Wisniewski et al. |
| 2012/0295328 A1 | 11/2012 | Wyrich |
| 2013/0144049 A1 | 6/2013 | Yoshimoto et al. |
| 2013/0323815 A1 | 12/2013 | Gundling et al. |
| 2014/0051844 A1 | 2/2014 | Forman et al. |
| 2014/0227691 A1 | 8/2014 | May et al. |
| 2015/0353920 A1 | 12/2015 | Enderle et al. |
| 2016/0326516 A1* | 11/2016 | Holmberg ............ B01L 3/5025 |

FOREIGN PATENT DOCUMENTS

| | | |
|---|---|---|
| WO | WO 2012028737 A1 | 3/2012 |
| WO | WO-2013045434 A1 | 4/2013 |
| WO | WO-2014122288 A1 | 8/2014 |

OTHER PUBLICATIONS

Chan K.C., et al., "Size Distributions of Maternal and Fetal DNA in Maternal Plasma," Clinical Chemistry, 2004, vol. 50 (1), pp. 88-92.

Chiu R.W., et al., "Maternal Plasma DNA Analysis with Massively Parallel Sequencing by Ligation for Noninvasive Prenatal Diagnosis of Trisomy 21," Clinical Chemistry, 2010, vol. 56 (3), pp. 459-463.

Chiu R.W., et al., "Non-Invasive Prenatal Assessment of Trisomy 21 by Multiplexed Maternal Plasma DNA Sequencing: Large Scale Validity Study," BMJ (Clinical Research Ed.), 2011, vol. 342, p. c7401.

Deangelis M.M., et al., "Solid-Phase Reversible Immobilization for the Isolation of PCR Products," Nucleic Acids Research, 1995, vol. 23 (22), pp. 4742-4743.

Fan H-M.C., et al., "Molecular Counting: From Noninvasive Prenatal Diagnostics to Whole-Genome Haplotyping," Thesis (Ph.D.)—Stanford University, 2011, 168 pages.

Gahan P.B., et al., "Circulating Nucleic Acids in Plasma and Serum: Applications in Diagnostic Techniques for Noninvasive Prenatal Diagnosis," International Journal of Women'S Health, 2013, vol. 5 (1), pp. 177-186.

Guibert J., et al., "Kinetics of Sry Gene Appearance in Maternal Serum: Detection by Real Time Pcr in Early Pregnancy After Assisted Reproductive Technique," Human Reproduction (Oxford, England), 2003, vol. 18 (8), pp. 1733-1736.

Holmberg R.C., et al., "Akonni Trutip(®) and Qiagen(®) Methods for Extraction of Fetal Circulating DNA—Evaluation by Real-Time and Digital Pcr," Plos One, 2013, vol. 8 (8), p. e73068.

International Search Report and Written Opinion for Application No. PCT/US2015/057179, dated Mar. 2, 2016, 14 pages.

Lis J.T., et al., "Size Fractionation of Double-stranded DNA by Precipitation With Polyethylene Glycol," Nucleic Acids Research, 1975, vol. 2<gs id="2978b685-66cf-4daf-9281-3bc0a5295b92" ginger_software_uiphraseguid="b6325c21-1f01-4eb7-90c9-2c27361dbbd5" class="GINGER_SOFTWARE_mark">(</gs>3), pp. 383-390.

Lo Y.M., et al., "Maternal Plasma DNA Sequencing Reveals the Genome-Wide Genetic and Mutational Profile of the Fetus," Science Translational Medicine, 2010, vol. 2 (61), p. 61ra91.

Lo Y.M., et al., "Presence of Fetal DNA in Maternal Plasma and Serum," Lancet (London, England), 1997, vol. 350 (9076), pp. 485-487.

Lo Y.M., et al., "Quantitative Analysis of Fetal DNA in Maternal Plasma and Serum: Implications for Noninvasive Prenatal Diagnosis," American Journal of Human Genetics, 1998, vol. 62 (4), pp. 768-775.

Lun F.M., et al., "Microfluidics Digital PCR Reveals a Higher than Expected Fraction of Fetal DNA in Maternal Plasma," Clinical Chemistry, 2008, vol. 54 (10), pp. 1664-1672.

Merrifield R.B., et al., "Solid-Phase Peptide Synthesis. 3. an Improved Synthesis of Bradykinin," Biochemistry, 1964, vol. 3 (9), pp. 1385-1390.

Pel J., et al., "Nonlinear Electrophoretic Response Yields a Unique Parameter for Separation of Biomolecules," Proceedings of the National Academy of Sciences of the United States of America, 2009, vol. 106 (35), pp. 14796-14801.

Sambrook J., et al., eds., Molecular Cloning: A Laboratory Manual, 3rd Edition, Cold Spring Harbor Laboratory, 2001, Table of Contents.

Schwarzenbach A., et al., "Cell-Free Nucleic Acids as Biomarkers in Cancer Patients," Nature Reviews Cancer, 2011, vol. 11, pp. 426-437.

Wilson, et al., ed., Harrison's Principles of Internal Medicine, Twelfth Edition, Mc Graw Hill, New York, NY, 1991, pp. 21-46.

Supplementary Partial European Search Report of related EP 15852776. Completed Apr. 30, 2018, 14 pages.

Office Action issued in related Chinese Patent Application No. 201580070732.0, dated Dec. 28, 2018, 12 pages.

\* cited by examiner

ENRICHMENT OF SMALL NUCLEIC ACIDS

The present Application is a divisional of U.S. application Ser. No. 15/728,199 filed Oct. 9, 2017, which claims priority to U.S. application Ser. No. 14/921,751 filed Oct. 23, 2015, which claims priority to U.S. Provisional Application Ser. No. 62/068,443 filed Oct. 24, 2014, the entirety of each of which is herein incorporated by reference.

FIELD OF INVENTION

Provided herein is technology related to processing samples of nucleic acids and particularly, but not exclusively, to methods for enriching samples for small nucleic acids, such as small circulating cell-free DNA that finds use, e.g., in prenatal testing, oncology testing, and infectious disease applications.

BACKGROUND

Prenatal diagnosis or prenatal screening refers to testing for diseases or conditions in a fetus or embryo before it is born. The aim is to detect birth defects such as neural tube defects, Down syndrome, chromosome abnormalities, genetic diseases and other conditions, such as spina bifida, cleft palate, Tay Sachs disease, sickle cell anemia, thalassemia, cystic fibrosis, Muscular dystrophy, and fragile X syndrome. Screening can also be used for prenatal sex discernment. Common testing procedures include amniocentesis, ultrasonography including nuchal translucency ultrasound, serum marker testing, or genetic screening. In some cases, the tests are administered to diagnose high-risk pregnancies early so that delivery can be scheduled in a tertiary care hospital where the baby can receive appropriate care.

Diagnostic prenatal testing can be by invasive or non-invasive methods. An invasive method involves probes or needles being inserted into the uterus, e g amniocentesis, which can be done from about 14 weeks gestation, and usually up to about 20 weeks, and chorionic villus sampling, which can be done earlier (between 9.5 and 12.5 weeks gestation) but which may be slightly more risky to the fetus. Chorionic villi sample and amniocentesis have related miscarriage risks of approximately 1 in 100 pregnancies and 1 in 200 pregnancies, respectively. Less risky procedures for non-invasive prenatal diagnosis have been implemented in the US and other countries. These techniques include examinations of the woman's womb through ultrasonography and maternal serum screens. For example, blood tests for select trisomies based on detecting fetal DNA present in maternal blood have become available (e.g., tests for Down syndrome in the United States and tests for Down and Edwards syndromes in China). The presence of fetal DNA in maternal plasma was first reported in 1997, offering the possibility for non-invasive prenatal diagnosis simply through the analysis of a maternal blood sample (Lo et al (1997), *Lancet* 350: 485-487).

As technology progresses, tests will shift from current more risky tests to less risky non-invasive tests. Leading medical bodies (e.g., the American College of Obstetricians and Gynecologists, the American College of Medical Genetics and Genomics, and the Society of Maternal and Fetal Medicine) currently endorse non-invasive prenatal screening for high-risk pregnancies. In addition, several companies (e.g., Sequenom, Verinata, Ariosa, Natera) are offering aneuploid testing services (e.g., to detect trisomy of chromosomes 21, 18, 13, X, and Y) based on laboratory-developed tests (LDT) developed under the Clinical Laboratory Improvement Amendments (CLIA) program. Furthermore, several payors (e.g. BCBS, Kaiser) offer reimbursement for trisomy testing in the face of increasing consumer demand driven by the overwhelming desire by expectant mothers to opt for modern non-invasive testing alternatives.

One particularly advantageous non-invasive test involves the analysis of cell-free fetal DNA (cffDNA). In a particular application, non-invasive prenatal aneuploidy testing of cffDNA is predicated on detecting the small fractional excess of DNA exhibited in instances of aneuploidy (e.g., trisomy) compared to a normal euploid fetus. In these tests, trisomy detection represents a problem of distinguishing 3 copies from 2 copies of a chromosome in a mixture where approximately 90% of the sample is euploid (e.g., disomic).

However, in practice, circulating cffDNA constitutes a minor fraction (approximately 3% to 6% (see, e.g., Lo et al. (1998) *Am J Hum Genet* 62: 768) or up to 10% to 20% according to some measures (see, e.g., Lun et al (2008) *Clin Chem* 54: 1664) of the total cell-free DNA in maternal plasma. In general, fractional circulating cffDNA concentration averages approximately 10% in early pregnancy (see, e.g., Chiu et al (2011) *BMJ* 342: c7401). This limitation poses a considerable challenge for non-invasive prenatal testing strategies that rely on direct chromosome enumeration methods for detecting fetal aneuploidy status (such as digital PCR, next-generation sequencing, or mass spectrometry).

For instance, assuming a 10% fetal DNA content in maternal plasma, the fractional increase of DNA in a fetal trisomy (e.g., involving chromosome 13, 18, 21, X, Y, or another chromosome) compared to a normal fetus is expected to be 1.05 (that is, 21 total copies for a trisomy compared to 20 copies for euploidy). This subtle difference in DNA content is measured by ultra-high density statistical counting methods that discriminate between the 1 and 1.05 ratio values observed in normal euploid and trisomic pregnancy cases, respectively.

In the routine clinical setting, the fetal DNA content of maternal plasma is commonly less than 10%, resulting in even smaller chromosomal disparities between trisomies and euploidies (e.g., ratios of approximately 1.02 to 1.03). The ability to enrich the cffDNA fraction by several-fold to modest levels (e.g., approximately 5-fold to 10-fold enrichment resulting in approximately 25% to 40% fetal DNA content) reduces the coverage and/or partition requirements for NGS and digital PCR applications, respectively (e.g., decreases the "digital real estate" associated with the technologies). Fetal DNA enrichment also facilitates fetal aneuploidy detection by mass spectrometry-based methods. Consequently, technologies are needed to enrich maternal blood samples for cffDNA to improve prenatal non-invasive diagnostic testing.

SUMMARY

Apoptotic fetal trophoblasts shed cffDNA directly into maternal blood in the placenta during gestation. It is estimated that cffDNAs are liberated into maternal plasma at a rate of approximately 20,000 per minute in 2.5 liters of maternal plasma (approximate total blood volume of a typical female is 5 liters) and are detected by some tests in circulating maternal plasma by approximately the 10th or 11th week of gestation and, in some studies, as early as the 5th week (see, e.g., Holmberg et al (2013), *PLoS One* 8(8):e73068) or, by some tests, as early as the 18th day of gestation (see, e.g., Guibert et al (2003) *Hum Reprod*

18:1733-6). A quasi-steady state relationship exists between cffDNA biogenesis in maternal plasma and cffDNA degradation by maternal plasma nucleases. As a result of these competing processes, it is estimated that cffDNA has a half-life of approximately 16 minutes in maternal plasma, which corresponds to approximately $7 \times 10^5$ copies of cffDNA in total maternal circulation at any given time or approximately 300 copies per milliliter of maternal blood. Thus, any particular cffDNA molecule is cleared from maternal plasma to undetectable levels within approximately 24 hours of its delivery to the maternal plasma. As a result, cffDNA is cleared from the maternal plasma within approximately 24 hours of childbirth and is thus associated with one pregnancy. In addition, compared to adult maternal DNA, fetal DNA is generally expected to be widely and actively transcribed during the gestational development program, suggesting that it may be more accessible (e.g., structurally unwound and de-condensed) and less-complexed with histones than maternal DNA. The net effect is that cffDNA is distinguishable from cell-free circulating maternal DNA by its smaller physical size distribution (see, e.g., Chan et al (2004) Clin Chem 50: 88-92; Lo et al (2010) Sci Transl Med 2).

In general, cffDNA is present predominantly at sizes of approximately 100 bp, bases, or nt to 200 bp, bases, or nt. Approximately 99% of fetal DNA has a length shorter than approximately 350 bp, bases, or nt (see, e.g., Chan et al. (2004) Clinical Chemistry 50(1): 88) and many recent studies indicate that fetal DNA generally tends to be less than approximately 300 bp, bases, or nt in size and maternal DNA is greater than 300 bp, bases, or nt in size (see, e.g., Gahan (2013) Int J Womens Health 5: 177-186). The technology provided herein exploits differences in DNA size distribution to enrich samples obtained from maternal blood for fetal DNA.

Accordingly, provided herein is technology for selectively isolating and enriching small cell-free circulating fetal nucleic acid (e.g., DNA or RNA), e.g., comprising less than approximately 100 bp, bases, or nt to 200 bp, bases, or nt, such as the cffDNA that is present in the maternal plasma of pregnant women at approximately 10 to 11 weeks gestation, from the background of higher molecular weight maternal cell-free circulating DNA (e.g., comprising more than approximately 200 bp, bases, or nt).

In general, the technology provides methods for the selective enrichment of low-molecular weight nucleic acids (e.g., DNA or RNA) from a complex distribution of higher molecular weight nucleic acids. Accordingly, the technology finds use in some embodiments to detect, quantify, and characterize circulating cell-free DNA that does not originate from a fetus, e.g., in a male, in a non-pregnant female, or in a pregnant female for a use other than for pre-natal testing of a fetus, e.g., to assess the medical status of the adult male or female. The technology finds use in the non-invasive analysis of circulating cell-free nucleic acids (e.g., DNA or RNA) in the diagnosis, assessment, treatment, and monitoring of cancer, liver disease, cardiovascular (e.g., heart) disease, kidney disease, inflammatory disease, and pulmonary disease in a subject. For example, the technology finds use in detecting, quantifying, and characterizing a biomarker (e.g., the technology finds use in detecting, quantifying, and characterizing methylated Septin 9 (ms9)) for colorectal cancer detection and screening, e.g., as provided by a bisulfite PCR assay (e.g., as provided commercially by the Abbott Molecular mS9 bisulfite PCR assay, e.g., on a m2000rt real-time PCR platform).

Further, the technology finds use in selectively isolating and enriching small cell-free circulating fetal nucleic acid (e.g., DNA or RNA) fragments from other biological samples, e.g., urine, cerebrospinal fluid (CSF), and peritoneal fluid.

The technology finds use in facilitating the non-invasive prenatal analysis of cell-free circulating fetal nucleic acid derived directly from maternal plasma samples, e.g., obtained after 5 weeks of gestation, e.g., at 10 to 11 weeks of gestation. Fetal nucleic acid enrichment reduces the statistical counting burden imposed by routine chromosome enumeration methods for aneuploidy analysis and detection, e.g., PCR (e.g., digital PCR), mass spec, and/or next generation sequencing (e.g., high-throughput shotgun sequencing, next-generation sequencing). That is, enrichment of maternal plasma samples for fetal nucleic acids provides a method in which less nucleic acid is evaluated than in existing methods—e.g., fewer total fetal and maternal chromosomes, alleles, markers, and/or nucleic acid molecules are counted to detect a euploid (ratio of 1.00) or aneuploid ratio (ratio that is not 1, e.g., a ratio that is greater than 1.00). In particular, methods for aneuploidy detection comprise quantifying maternal and fetal alleles, chromosomes, nucleic acid molecules, and/or markers and calculating ratios of fetal to maternal alleles, chromosomes, nucleic acid molecules, and/or markers to distinguish 3 copies from 2 copies of a fetal chromosome or chromosomal fragment. In a mixture where approximately 90% or more of the sample is euploid nucleic acid from the mother (e.g., disomic) and 10% fetal nucleic acid, the fractional increase of nucleic acid (e.g., DNA) in a fetal trisomy compared to a normal fetus is expected to be 1.05 (that is, 21 total copies for a trisomy compared to 20 copies for euploidy). Consequently, enumeration of a large number of alleles, chromosomes, nucleic acid molecules, and/or markers is required to provide statistically significant discrimination of a value of 1.05 from a value of 1.00. As the fraction of fetal nucleic acid decreases in the sample (e.g., to less than 10%), the ratio that is indicative of aneuploid status decreases, e.g., to 1.04, 1.03, 1.02, etc., which are values that require very sensitive detection and even more extensive enumeration to provide statistically significant discrimination from a value of 1.00.

In contrast, in an enriched sample comprising greater than 10% fetal nucleic acid (e.g., as provided by the present technology), the ratio indicating aneuploidy is increasingly more than 1.05 (e.g., 1.06, 1.07, 1.08, 1.09, 1.1, 1.2, 1.3, 1.4, 1.5). Accordingly, fewer alleles, chromosomes, nucleic acid molecules, and/or markers are enumerated to provide a statistically significant indication that the value is 1.00 (indicative of euploidy) or greater than 1.00 (indicative of aneuploidy). Moreover, additional enumeration provides greater confidence of the discrimination between a value that is 1.00 and a value that is greater than 1.00. As such, the technology provides methods for discriminating an aneuploid ratio from a euploid ratio based on enumeration of fewer total fetal and maternal chromosomes, alleles, markers, and/or nucleic acid molecules relative to existing technologies.

The reduced statistical counting burden translates to shorter effective assay turn-around times (e.g., improving digital PCR and next-generation sequencing applications), increased sensitivity, increased throughput by increased multiplexing of patient samples, and expanded coverage of assays, e.g., to encompass or include additional chromosomal or sub-chromosomal targets and/or markers. For next-generation sequencing-based methods, the assay non-validity rate (e.g., the no-call rate or invalidity rate) is improved by minimizing the number of sequence tags (e.g., sequence reads) necessary for enumerating an accurate call.

Accordingly, some embodiments of the technology provide a method for producing an output sample comprising an increased concentration of small nucleic acids (e.g., DNA (e.g., cffDNA) and/or RNA) compared to an input sample, the method comprising one or more of: (a) eluting small nucleic acid fragments preferentially from silica; (b) retaining large nucleic acid fragments preferentially on silica; (c) enriching small nucleic acid based on differences in methylation relative to other nucleic acid (e.g., by methylated DNA immunoprecipitation (MeDIP, e.g., as provided by Cyprus Genetics) (e.g., with antibody-coated particles that are captured by a magnetic field (e.g., paramagnetic or magnetic particles) or capture on a solid support (e.g., onto an affinity column (e.g., an antibody-coated spin column, e.g., as provided by Molzyme) or other solid support such as, e.g., a microtiter plate, bead, slide, nanostructure, etc.)); (d) enriching small nucleic acid by size exclusion; (e) enriching small nucleic acids by synchronous (or non-synchronous) coefficient of drag alteration sizing (SCODA, e.g., as provided by Boreal Genomics); (f) enriching small nucleic acids by solid phase reversible immobilization sizing (e.g., using carboxylated magnetic beads); (g) enriching small nucleic acids by electrophoresis-based sizing; (h) enriching small nucleic acids by affinity chromatography using iron oxide; (i) enriching small nucleic acids by affinity chromatography, e.g., the affinity of a nucleic acid for a positively charged substrate (e.g., a polycation, a metal ion (e.g., a chelated metal ion, e.g., a composition comprising multiple chelated metal ions), a composition comprising hydroxyapatite, or hydroxyapatite coated magnetic particles); or (j) enriching small nucleic acids by use of simultaneous anion exchange and size exclusion (e.g., using microparticles comprising an anion exchange functional group (e.g., an amine, e.g., a weak amine) and surface irregularities that create micron and sub-micron sized pores that are accessible to target (e.g., small) nucleic acids), wherein processing the input sample with one or more of these techniques produces an output sample comprising a higher concentration of small nucleic acids than the concentration of small nucleic acids in the input sample.

Some related embodiments provide a method for evaluating a blood sample comprising fetal nucleic acids (e.g. DNA and/or RNA), the method comprising 1) obtaining a blood sample from a pregnant woman; 2) producing an output sample from the blood sample using one or more of: a) eluting small nucleic acids preferentially from silica; b) retaining large nucleic acids preferentially on silica; c) enriching small nucleic acids by methylated DNA immunoprecipitation or capture with antibody-coated particles that are captured by a magnetic field (e.g., paramagnetic or magnetic particles); d) enriching small nucleic acids by size exclusion; e) enriching small nucleic acids by coefficient of drag alteration sizing; f) enriching small nucleic acids by solid phase reversible immobilization sizing; g) enriching small nucleic acids by electrophoresis-based sizing; h) enriching small nucleic acids by affinity chromatography using iron oxide; i) enriching small nucleic acids by affinity chromatography, e.g., the affinity of a nucleic acid for a positively charged substrate (e.g., a polycation, a metal ion (e.g., a chelated metal ion, e.g., a composition comprising multiple chelated metal ions), a composition comprising hydroxyapatite, or hydroxyapatite coated magnetic particles); or enriching small nucleic acids by use of simultaneous anion exchange and size exclusion (e.g., using microparticles comprising an anion exchange functional group (e.g., an amine, e.g., a weak amine) and surface irregularities that create micron and sub-micron sized pores that are accessible to target (e.g., small) nucleic acids), and 3) testing the small nucleic acids for a genetic abnormality, wherein processing the blood sample with one or more of these techniques produces an output sample comprising a higher concentration of small nucleic acids than the concentration of small nucleic acids in the blood sample.

In some embodiments, methods further comprise minimizing and/or eliminating lysis of maternal cells to minimize and/or eliminate maternal nucleic acid in the sample. For example, minimizing the time a sample is stored, minimizing processing time, adding a reagent to stabilize cells (e.g., prevent lysis (e.g., prevent lysis of maternal white blood cells)), using a cell-stabilizing tube, adding a preservative, removing maternal cells, minimizing physical movement of the sample (e.g., handling, agitation, transport), minimizing temperature changes, and encapsulating maternal cells.

In some embodiments, the methods are automated through use of robotics and other apparatuses (e.g., a programmable and/or computer-controlled apparatus). In some embodiments, the methods find use in a microfluidic apparatus.

Some embodiments of the technology provide a method for producing an output sample comprising an increased concentration of small nucleic acids relative to an input sample, the method comprising combining one or both of: A) eluting small nucleic acids fragments preferentially from silica and/or retaining large nucleic acids fragments preferentially on silica; with one or more of: B) enriching by methylated DNA immunoprecipitation or capture with antibody-coated particles that are captured by a magnetic field (e.g., paramagnetic or magnetic particles) or affinity columns; enriching by size exclusion; enriching by coefficient of drag alteration sizing; enriching by solid phase reversible immobilization sizing; enriching by electrophoresis-based sizing; and/or enriching by combined anion exchange and size exclusion, wherein processing the input sample with one or more of the silica based techniques combined with one or more of enrichment techniques produces an output sample comprising a higher concentration of small nucleic acids than the concentration of small nucleic acids in the input sample.

In some embodiments, eluting small nucleic acids preferentially from silica comprises eluting in 5 to 25% ethanol, 5 to 25% methanol, 5 to 25% acetonitrile, 5 to 25% DMSO, 1 to 25% formamide, greater than 1 M NaCl, a high concentration of a chaotropic salt; eluting at a temperature lower than 16° C. or eluting at a pH at or below the pKa of the surface silanol groups of the silicon surface; electroeluting small nucleic acids by continuous forward-field electro-elution, continuous reverse-field electro-elution, or oscillating-field electro-elution; and/or using an ion exchange column. In some embodiments, retaining large nucleic acids preferentially on silica comprises treating the silica with a polymer coating, volume-exclusion agent, or absorptive agent, doping the silica membrane with an amine-binding surface doping agent or a polyphosphate-binding surface doping agent; and/or cross-linking large nucleic acids with ultraviolet radiation, by forming thymidine dimers, by use of psoralen, or with a chemical cross-linking agent (e.g., formalin, alkylating agents (e.g., 1,3-bis(2-chloroethyl)-1-nitrosourea (BCNU, carmustine)), nitrogen mustard, cisplatin, nitrous acid, aldehydes (e.g., malondialdehyde, acrolein, crotonaldehyde), chloroethylating agents, nitrosoureas, triazenes, alkyl sulfonates, epoxides, diepoxybutane, carzinophilin, azinomycin B, cis-Diamminedichloroplatinum (II), sandramycin, luzopeptins, isochrysohermidin, pyrrolobenzodiazepine agents, cyclophosphamide, N,N,N,N',N',N'-hexamethylmelamines, pyrrolizidine alkaloids, anthracyclines, mitomycin C, aziridinylbenzoquinones, biselezin). In some embodiments, retaining large nucleic acids preferentially on silica comprises treating the silica with 0.5 to 2% acrylamide/bis-acrylamide comprising a 19:1 to 29:1 cross-linking ratio, 0.01 to 0.5% agarose, 0.01 to 1.0% polyethylene glycol having an average molecular weight of 1000 to 10,000, 1 to 10% dextran sulfate, 1 to 10% ficoll, 1 to 10% sorbitol, 1 to 10% aldohexose polymer, 1 to 10% polyvinyl alcohol, 1 to 10% polyamines, nylon, polyester, or polystyrene. In some embodiments, retaining large nucleic acids preferentially on silica comprises cross-linking large nucleic acids with a cross linking agent (e.g., formalin, alkylating agents (e.g., 1,3-bis(2-chloroethyl)-1-nitrosourea (BCNU, carmustine)), nitrogen mustard, cisplatin, nitrous acid, aldehydes (e.g., malondialdehyde, acrolein, crotonaldehyde), chloroethylating agents, nitrosoureas, triazenes, alkyl sulfonates, epoxides, diepoxybutane, carzinophilin, azinomycin B, cis-Diamminedichloroplatinum (II), sandramycin, luzopeptins, isochrysohermidin, pyrrolobenzodiazepine agents, cyclophosphamide, N,N,N,N',N',N'-hexamethylmelamines, pyrrolizidine alkaloids, anthracyclines, mitomycin C, aziridinylbenzoquinones, biselezin) or a DTT-cleavable, thiol-labile bis-acrylamide/acrylamide mixture.

In some embodiments, small DNA is enriched based on it having a different methylation status relative to other DNA. In some embodiments, enriching based on methylation status comprises use of agents that are specific for methylated DNA relative to non-methylated DNA (e.g., an antibody recognizing methylated DNA, e.g., an antibody specific for methyl-cytosine or an antibody specific for methyl-cytosine in a CpG dinucleotide, e.g., in a CpG island). In some embodiments enriching based on methylation status comprises use of a solid support comprising (e.g., linked to) an agent that is specific for methylated DNA relative to non-methylated DNA (e.g., an antibody recognizing methylated DNA, e.g., an antibody specific for methyl-cytosine or an antibody specific for methyl-cytosine in a CpG dinucleotide, e.g., in a CpG island). In some embodiments, the solid support is an affinity column (e.g., in some embodiments enriching based on methylation status comprises use of an affinity column comprising (e.g., linked to) an agent that is specific for methylated DNA relative to non-methylated DNA (e.g., an antibody recognizing methylated DNA, e.g., an antibody specific for methyl-cytosine or an antibody specific for methyl-cytosine in a CpG dinucleotide, e.g., in a CpG island)).

In some embodiments, enriching based on methylation status comprises use of methylated DNA immunoprecipitation (MeDIP), e.g., using an antibody-coated solid support (e.g., antibody-coated particles that are captured by a magnetic field (e.g., antibody-coated paramagnetic particles or antibody-coated magnetic particles)) and a method that comprises: incubating the eluate from a silica-based isolation method with the solid support (e.g., antibody-coated particles that are captured by a magnetic field (e.g., antibody-coated paramagnetic particles or antibody-coated magnetic particles)) functionalized with an antibody that recognizes methylated DNA; eluting the small DNA from the solid support (e.g., antibody-coated paramagnetic particles or antibody-coated magnetic particles)) using excess 5-methylcytosine, using heat denaturation, or using inactivation of the antibody; and/or purifying or amplifying the small DNA.

In some embodiments, enriching by size exclusion comprises using ultrafiltration, size-exclusion chromatography, use of beads having an irregular surface, or dialysis. In some embodiments, enriching by solid phase reversible immobilization sizing comprises use of a crowding agent. In some embodiments, methods comprise use of PEG at a concentration of less than 5.1% weight per volume or less than 4.8% weight per volume. In some embodiments methods comprise use of PEG 8000. In some embodiments, methods comprise use of PEG 8000 (e.g., PEG having an average molecular weight of approximately 8000) at a concentration of less than 10%, 9%, 8%, 7%, 6%, e.g., less than 5.1% weight per volume, e.g., less than 4.8% weight per volume. In some embodiments, enriching by electrophoresis comprises use of agarose gel electrophoresis, acrylamide gel electrophoresis, or capillary electrophoresis. In some embodiments, eluting small nucleic acids preferentially from silica comprises the use of magnetic beads. For example, some embodiments comprise a size selection using magnetic bead purification and control of binding buffer composition. In some embodiments, PEG 8000 is used as a binding buffer with the magnetic beads and the concentration of PEG is adjusted to provide the desired size selection. In particular, the higher the percentage of PEG in the binding buffer, the more DNA is bound to the beads. Also, decreasing the percentage of PEG promotes the binding of larger DNA and hinders the binding of the smaller fragments.

The technology is adaptable to a range of cutoff values for differentiating small DNA from large DNA. For example, PEG concentration can be adjusted to provide for the desired cutoff (e.g., using PEG (e.g., PEG 8000) concentrations of 4 to 5%, e.g., 4.0%, 4.1%, 4.2%, 4.3%, 4.4%, 4.5%, 4.6%, 4.7%, 4.8%, 4.9%, or 5.0%). Accordingly, embodiments provide methods for enriching a sample for small DNA, wherein small DNA is DNA having a length less than a length cutoff value of 1000, 900, 800, 700, 600, 500, 400, 300, 275, 250, 225, 200, 175, 150, 125, 100, 75, or 50 base pairs, bases, or nucleotides. In some embodiments, the distribution and relative abundance of fragment sizes smaller than a length cutoff value in the output sample and the distribution and relative abundance of fragment sizes of fragment sizes smaller than a length cutoff value in the input sample are the same or similar. In some embodiments, a higher concentration of PEG (e.g., PEG 8000) is used, e.g., 15% to 20% (e.g., 15%, 16%, 17%, 18%, 19%, or 20%).

Accordingly, some embodiments of the technology provide a method for producing an output sample comprising an increased concentration of small nucleic acids (e.g., DNA (e.g., cffDNA) and/or RNA) compared to an input sample, the method comprising eluting small nucleic acids preferentially from a substrate that has affinity for nucleic acids. For example, some embodiments enrich a sample for small nucleic acids by affinity chromatography, e.g., by a method based on the affinity of a nucleic acid for a positively charged substrate (e.g., a polycation, a metal ion (e.g., a chelated metal ion, e.g., a composition comprising multiple chelated metal ions), a composition comprising hydroxyapatite, or hydroxyapatite coated magnetic particles). In some embodiments, the method comprises eluting small nucleic acids from one or more of iron oxide, hydroxyapatite, and/or hydroxyapatite-coated magnetic particles using solutions of a phosphate containing counter ion at concentrations that selectively elute small DNA as compared to higher molecular weight fractions of DNA.

In some embodiments, the technology provides a method for producing an output sample comprising an increased concentration of small nucleic acids relative to an input sample. In particular, methods comprise providing an input sample (e.g., a biological sample, e.g., a blood sample or a sample derived from a blood sample) comprising nucleic acids (e.g., comprising small nucleic acids); incubating the input sample with a SPRI substrate (e.g., beads, e.g., magnetic beads, e.g., carboxylated paramagnetic beads) and a crowding agent (e.g., PEG, e.g., PEG 8000) to produce a bound fraction comprising large nucleic acids and a supernatant fraction comprising small nucleic acids; and removing the supernatant fraction to produce an output sample comprising small nucleic acids (e.g., at a concentration greater than the concentration of small nucleic acids in the input sample). In some embodiments, methods comprise providing an input sample (e.g., a biological sample, e.g., a blood sample or a sample derived from a blood sample) comprising small nucleic acids; incubating the input sample with carboxylated paramagnetic beads and PEG having an average molecular weight of approximately 8000 to produce a bound fraction comprising large nucleic acids and a supernatant fraction comprising small nucleic acids; and removing the supernatant fraction to produce an output sample comprising small nucleic acids (e.g., at a concentration greater than the concentration of small nucleic acids in the input sample). In some embodiments, the technology provides methods comprising providing an input sample (e.g., a biological sample, e.g., a blood sample or a sample derived from a blood sample) comprising small nucleic acids; incubating the input sample with carboxylated paramagnetic beads and PEG having an average molecular weight of approximately 8000 and a concentration of 4% to 5% weight to volume to produce a bound fraction comprising large nucleic acids and a supernatant fraction comprising small nucleic acids; and removing the supernatant fraction to produce an output sample comprising small nucleic acids (e.g., at a concentration greater than the concentration of small nucleic acids in the input sample).

In some embodiments, the technology provides methods comprising providing an input sample (e.g., a blood sample or a sample derived from a blood sample) comprising small nucleic acids; incubating the input sample with carboxylated paramagnetic beads and PEG having an average molecular weight of approximately 8000 and a concentration of approximately 4.8% weight to volume to produce a bound fraction comprising large nucleic acids and a supernatant fraction comprising small nucleic acids having a size that is less than or equal to approximately 1000 bp, bases, or nt; and removing the supernatant fraction to produce an output sample comprising small nucleic acids (e.g., at a concentration greater than the concentration of small nucleic acids in the input sample).

In some embodiments, the technology provides methods comprising providing an input sample (e.g., a biological sample, e.g., a blood sample or a sample derived from a blood sample) comprising small nucleic acids; incubating the input sample with carboxylated paramagnetic beads and PEG having an average molecular weight of approximately 8000 and a concentration of approximately 5.1% weight to volume to produce a bound fraction comprising large nucleic acids and a supernatant fraction comprising small nucleic acids having a size that is less than or equal to approximately 600 bp, bases, or nt; and removing the supernatant fraction to produce an output sample comprising small nucleic acids (e.g., at a concentration greater than the concentration of small nucleic acids in the input sample).

In some embodiments, the technology provides methods comprising providing an input sample (e.g., a biological sample (e.g., a blood sample, a urine sample, a peritoneal fluid sample, a cerebrospinal fluid sample, or a sample derived or isolated from a blood sample, a urine sample, a peritoneal fluid sample, or a cerebrospinal fluid sample) comprising small nucleic acids; incubating the input sample with a solid support (e.g., beads, e.g., magnetic beads, e.g., carboxylated paramagnetic beads) and a crowding agent (e.g., PEG, e.g., PEG having an average molecular weight of approximately 5000 to 10,000; e.g., PEG having an average molecular weight of approximately 5000; 6000; 7000; 8000; 9000; or 10,000) at a concentration of approximately 4.0% to 6.0% (e.g., 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%) weight to volume to produce a bound fraction comprising large nucleic acids and a supernatant fraction comprising small nucleic acids having a size that is less than or equal to approximately 500 to 1200 bp, bases, or nt (e.g., 500, 550, 600, 650, 700, 750, 800, 850, 900, 950, 1000, 1050, 1100, 1150, 1200 bp, bases, or nt); and removing the supernatant fraction to produce an output sample comprising small nucleic acids (e.g., at a concentration greater than the concentration of small nucleic acids in the input sample).

In some embodiments, said methods comprising incubating a sample with a solid support and a crowding agent as described above additionally include one or more of: (a) eluting small nucleic acid fragments preferentially from silica; (b) retaining large nucleic acid fragments preferentially on silica; (c) enriching small nucleic acid based on differences in methylation relative to other nucleic acid (e.g., by methylated DNA immunoprecipitation (MeDIP, e.g., as provided by Cyprus Genetics) (e.g., with antibody-coated particles that are captured by a magnetic field (e.g., paramagnetic or magnetic particles) or capture on a solid support (e.g., onto an affinity column (e.g., an antibody-coated spin column, e.g., as provided by Molzyme) or other solid support such as, e.g., a microtiter plate, bead, slide, nanostructure, etc.)); (d) enriching small nucleic acid by size exclusion; (e) enriching small nucleic acids by synchronous (or non-synchronous) coefficient of drag alteration sizing (SCODA, e.g., as provided by Boreal Genomics); (f) enriching small nucleic acids by solid phase reversible immobilization sizing (e.g., using carboxylated magnetic beads); (g) enriching small nucleic acids by electrophoresis-based sizing; (h) enriching small nucleic acids by affinity chromatography using iron oxide; (i) enriching small nucleic acids by affinity chromatography, e.g., the affinity of a nucleic acid for a positively charged substrate (e.g., a polycation, a metal ion (e.g., a chelated metal ion, e.g., a composition comprising multiple chelated metal ions), a composition comprising hydroxyapatite, or hydroxyapatite coated magnetic particles); or (j) enriching small nucleic acids by use of simultaneous anion exchange and size exclusion (e.g., using microparticles comprising an anion exchange functional group (e.g., an amine, e.g., a weak amine) and surface irregularities that create micron and sub-micron sized pores that are accessible to target (e.g., small) nucleic acids).

The methods find use in non-invasive prenatal testing; thus, in some embodiments the input sample is a blood sample, a sample derived from, produced from, and/or comprising a blood sample, and/or the input sample is provided by obtaining a blood sample from a pregnant woman. Additional embodiments provide a method for testing a subject for a chromosomal aberration, the method comprising testing the output sample for the chromosomal aberration. In some embodiments, the chromosomal aberration is an aneuploidy. The technology is not limited in the testing that is applied to the enriched sample for the pre-natal testing. For example, in some embodiments the testing comprises use of PCR (digital PCR, quantitative PCR, droplet digital PCR), digital counting by sequencing, sequencing (e.g., massively parallel sequencing, next-generation sequencing, high-throughput shotgun sequencing), and/or mass spectrometry. In some embodiments, the technology provides a sample enriched for small DNA produced by a method as described herein. In some embodiments, the ratio of small DNA in the output sample relative to the small DNA in the input sample is 2, 5, 10, 50, or 100.

Moreover, in some embodiments, the technology provides a method for producing an output sample comprising an increased concentration of small DNA relative to an input sample (e.g., the ratio of small DNA in the output sample relative to the small DNA in the input sample is 2, 5, 10, 50, or 100), the method comprising combining one or both of: A) eluting small nucleic acids preferentially from silica (e.g., comprising eluting in 5 to 25% ethanol, 5 to 25% methanol, 5 to 25% acetonitrile, 5 to 25% DMSO, 1 to 25% formamide, greater than 1 M NaCl, a high concentration of a chaotropic salt; eluting at a temperature lower than 16° C. or eluting at a pH at or below the pKa of the surface silanol groups of the silicon surface; electroeluting small nucleic acids by continuous forward-field electro-elution, continuous reverse-field electro-elution, or oscillating-field electro-elution; and/or using an ion exchange column); and/or retaining large nucleic acids preferentially on silica (e.g., comprising treating the silica with a polymer coating, volume-exclusion agent, or absorptive agent, doping the silica membrane with an amine-binding surface doping agent or a polyphosphate-binding surface doping agent; and/or cross-linking large nucleic acids with ultraviolet radiation, by forming thymidine dimers, by use of psoralen, or with a chemical cross-linking agent (e.g., formalin, alkylating agents (e.g., 1,3-bis(2-chloroethyl)-1-nitrosourea (BCNU, carmustine)), nitrogen mustard, cisplatin, nitrous acid, aldehydes (e.g., malondialdehyde, acrolein, crotonaldehyde), chloroethylating agents, nitrosoureas, triazenes, alkyl sulfonates, epoxides, diepoxybutane, carzinophilin, azinomycin B, cis-Diamminedichloroplatinum (II), sandramycin, luzopeptins, isochrysohermidin, pyrrolobenzodiazepine agents, cyclophosphamide, N,N,N,N',N',N'-hexamethylmelamines, pyrrolizidine alkaloids, anthracyclines, mitomycin C, aziridinylbenzoquinones, biselezin); comprising treating the silica with 0.5 to 2% acrylamide/bis-acrylamide comprising a 19:1 to 29:1 cross-linking ratio (and, optionally, employing a DTT-cleavable, thiol-labile bis-acrylamide cross-linker), 0.01 to 0.5% agarose, 0.01 to 1.0% polyethylene glycol having an average molecular weight of 1000 to 10,000, 1 to 10% dextran sulfate, 1 to 10% ficoll, 1 to 10% sorbitol, 1 to 10% aldohexose polymer, 1 to 10% polyvinyl alcohol, 1 to 10% polyamines, nylon, polyester, or polystyrene; comprising cross-linking large nucleic acids with a cross-linking agent (e.g., formalin, alkylating agents (e.g., 1,3-bis(2-chloroethyl)-1-nitrosourea (BCNU, carmustine)), nitrogen mustard, cisplatin, nitrous acid, aldehydes (e.g., malondialdehyde, acrolein, crotonaldehyde), chloroethylating agents, nitrosoureas, triazenes, alkyl sulfonates, epoxides, diepoxybutane, carzinophilin, azinomycin B, cis-Diamminedichloroplatinum (II), sandramycin, luzopeptins, isochrysohermidin, pyrrolobenzodiazepine agents, cyclophosphamide, N,N,N,N',N',N'-hexamethylmelamines, pyrrolizidine alkaloids, anthracyclines, mitomycin C, aziridinylbenzoquinones, biselezin); with one or more of: B) enriching by methylated DNA immunoprecipitation with antibody-coated particles that can be captured with a magnetic field (e.g., antibody-coated paramagnetic particles or antibody-coated magnetic particles)) (e.g., comprising incubating the eluate from a silica-based isolation method with paramagnetic beads functionalized with an antibody recognizing methylated DNA; eluting the small DNA from the paramagnetic beads using excess 5-methylcytosine, using heat denaturation, using inactivation of the antibody; and purifying or amplifying the small DNA); enriching by size exclusion (e.g., using ultrafiltration, size-exclusion chromatography, or dialysis; using a crowding agent; using PEG (e.g., PEG 8000) at a concentration of less than 5.1% weight per volume or less than 4.8% weight per volume; using agarose gel electrophoresis, acrylamide gel electrophoresis, or capillary electrophoresis); enriching by coefficient of drag alteration sizing; enriching by solid phase reversible immobilization sizing; and/or enriching by electrophoresis-based sizing, wherein processing the input sample with one or both of the silica based techniques combined with one or more of the enrichment techniques produces an output sample comprising a higher concentration of small DNA (e.g., having a length less than a length cutoff value of 1000, 900, 800, 700, 600, 500, 400, 300, 275, 250, 225, 200, 175, 150, 125, 100, 75, or 50 base pairs, bases, or nucleotides) than the concentration of small DNA in the input sample and wherein the distribution of fragment sizes and relative abundance of fragment sizes smaller than a length cutoff value in the output sample and the distribution of fragment sizes and relative abundance of fragment sizes smaller than a length cutoff value in the input sample are the same or similar.

In some embodiments, the technology provides a method for evaluating a blood sample comprising nucleic acids by obtaining a blood sample from a subject, producing an output sample comprising small nucleic acids from the blood sample, and testing the small nucleic acids. In some embodiments, producing the output sample uses methods comprising various permutations and/or combinations of; eluting small nucleic acids preferentially from silica, retaining large nucleic acids preferentially on silica, enriching small nucleic acids by methylated DNA immunoprecipitation with an antibody-coated solid support, enriching small nucleic acids by size exclusion, enriching small nucleic acids by coefficient of drag alteration sizing, enriching small nucleic acids by solid phase reversible immobilization sizing, enriching small nucleic acids by electrophoresis-based sizing, and enriching small nucleic acids by affinity chromatography. In some embodiments, the methods comprise permutations and/or combinations using any 2 of, any 3 of, any 4 of, any 5 of, any 6 of, any 7 of, or all 8 of eluting small nucleic acids preferentially from silica, retaining large nucleic acids preferentially on silica, enriching small nucleic acids by methylated DNA immunoprecipitation with an antibody-coated solid support, enriching small nucleic acids by size exclusion, enriching small nucleic acids by coefficient of drag alteration sizing, enriching small nucleic acids by solid phase reversible immobilization sizing, enriching small nucleic acids by electrophoresis-based sizing, and enriching small nucleic acids by affinity chromatography.

For example, in some embodiments the technology comprises enriching small nucleic acids using solid phase reversible immobilization (SPRI). In some embodiments comprising use of solid phase reversible immobilization, small nucleic acids are enriched using a solid support such as a bead (e.g., a paramagnetic bead comprising carboxylate groups), a crowding agent (e.g., PEG), and a salt (e.g., NaCl). In some embodiments comprising use of a solid support such as a bead (e.g., a magnetic (e.g., a paramagnetic) bead comprising carboxylate groups), a crowding agent (e.g., PEG (e.g., PEG 8000)) at approximately 3% to 8% (or 3%, 4% (e.g., 4.8%), 5% (e.g., 5.1%), e.g., 5.5%, 6%, 6.5%, 7%, 7.5%, etc.) weight per volume), and a salt (e.g., NaCl), large nucleic acids are preferentially bound to the solid support, thus enriching the surrounding buffer with small nucleic acids (e.g., nucleic acids less than 500 bases, bp, or nt (e.g., less than 450, 400, 350, 300, 250, 200, 150, or 100 bases, bp, or nt).

In some embodiments, the technology comprises enriching small nucleic acids using a silica column and wash buffers that promote the binding of large nucleic acids to the silica columns and promote the small nucleic acids to wash off the column in the wash buffer. For example, in some embodiments, small nucleic acids are enriched by using a silica column and a wash buffer comprising 70% EtOH and a ratio of wash buffer volume to sample volume of approximately 0.5 to 1 to 0.4 to 1. In some embodiments, the technology comprises enriching small nucleic acids using a silica column and a wash buffer comprising Tween-20, ethanol, and $MgCl_2$ (e.g., 10% Tween-20, 15% ethanol, and 20 mM $MgCl_2$) at a wash buffer volume to sample volume of approximately 0.5 to 1 to 0.4 to 1.

Thus, in some embodiments, the technology comprises enriching a sample for small nucleic acids (e.g., DNA) using a combination of enrichment by solid phase reversible immobilization (SPRI) and enrichment using a silica column. In some embodiments comprising enrichment by solid phase reversible immobilization and a silica column, a PEG buffer comprising approximately at least 4% to at least 5% PEG (e.g., PEG 8000 (e.g., 4.8% or 5.1% PEG 8000)) is used to increase recovery of small nucleic acids from the SPRI substrate and a wash buffer comprising ethanol (e.g., 70% ethanol) or a wash buffer comprising Tween-20, ethanol, and $MgCl_2$ (e.g., at a wash buffer volume to sample volume ratio of 0.5 to 1 to 0.4 to 1) is used to increase recovery of small nucleic acids from the silica column in the wash buffer. In some embodiments, the PEG buffer promotes binding of large nucleic acids to the SPRI substrate and thus promotes recovery of small nucleic acids in the flow-through, wash, and/or eluate. Similarly, in some embodiments the silica column wash buffer (e.g., comprising ethanol or comprising Tween-20, ethanol, and $MgCl_2$) promotes the binding of large nucleic acids to the silica substrate and thus promotes recovery of small nucleic acids in the wash.

In some embodiments, the methods comprise eluting small nucleic acids preferentially from silica and enriching small nucleic acids by methylated DNA immunoprecipitation with an antibody-coated solid support. In some embodiments, the methods comprise eluting small nucleic acids preferentially from silica and enriching small nucleic acids by size exclusion. In some embodiments, the methods comprise eluting small nucleic acids preferentially from silica and enriching small nucleic acids by coefficient of drag alteration sizing. In some embodiments, the methods comprise eluting small nucleic acids preferentially from silica and enriching small nucleic acids by solid phase reversible immobilization sizing. In some embodiments, the methods comprise eluting small nucleic acids preferentially from silica and enriching small nucleic acids by electrophoresis-based sizing. In some embodiments, the methods comprise eluting small nucleic acids preferentially from silica and enriching small nucleic acids by affinity chromatography.

In some embodiments, the methods comprise retaining large nucleic acids preferentially on silica and enriching small nucleic acids by methylated DNA immunoprecipitation with an antibody-coated solid support. In some embodiments, the methods comprise retaining large nucleic acids preferentially on silica and enriching small nucleic acids by size exclusion. In some embodiments, the methods comprise retaining large nucleic acids preferentially on silica and enriching small nucleic acids by coefficient of drag alteration sizing. In some embodiments, the methods comprise retaining large nucleic acids preferentially on silica and enriching small nucleic acids by solid phase reversible immobilization sizing. In some embodiments, the methods comprise retaining large nucleic acids preferentially on silica and enriching small nucleic acids by electrophoresis-based sizing. In some embodiments, the methods comprise retaining large nucleic acids preferentially on silica and enriching small nucleic acids by affinity chromatography.

In some embodiments, the methods comprise eluting small nucleic acids preferentially from silica and retaining large nucleic acids preferentially on silica. In some embodiments, the methods comprise eluting small nucleic acids preferentially from silica and enriching small nucleic acids by methylated DNA immunoprecipitation with an antibody-coated solid support. In some embodiments, the methods comprise eluting small nucleic acids preferentially from silica and enriching small nucleic acids by size exclusion. In some embodiments, the methods comprise eluting small nucleic acids preferentially from silica and enriching small nucleic acids by coefficient of drag alteration sizing. In some embodiments, the methods comprise eluting small nucleic acids preferentially from silica and enriching small nucleic acids by solid phase reversible immobilization sizing. In some embodiments, the methods comprise eluting small nucleic acids preferentially from silica and enriching small nucleic acids by electrophoresis-based sizing. In some embodiments, the methods comprise eluting small nucleic acids preferentially from silica and enriching small nucleic acids by affinity chromatography.

In some embodiments, the methods comprise retaining large nucleic acids preferentially on silica and eluting small nucleic acids preferentially from silica. In some embodiments, the methods comprise retaining large nucleic acids preferentially on silica and enriching small nucleic acids by methylated DNA immunoprecipitation with an antibody-coated solid support. In some embodiments, the methods comprise retaining large nucleic acids preferentially on silica and enriching small nucleic acids by size exclusion. In some embodiments, the methods comprise retaining large nucleic acids preferentially on silica and enriching small nucleic acids by coefficient of drag alteration sizing. In some embodiments, the methods comprise retaining large nucleic acids preferentially on silica and enriching small nucleic acids by solid phase reversible immobilization sizing. In some embodiments, the methods comprise retaining large nucleic acids preferentially on silica and enriching small nucleic acids by electrophoresis-based sizing. In some embodiments, the methods comprise retaining large nucleic acids preferentially on silica and enriching small nucleic acids by affinity chromatography.

In some embodiments, the methods comprise enriching small nucleic acids by methylated DNA immunoprecipitation with an antibody-coated solid support and eluting small nucleic acids preferentially from silica. In some embodiments, the methods comprise enriching small nucleic acids by methylated DNA immunoprecipitation with an antibody-coated solid support and retaining large nucleic acids preferentially on silica. In some embodiments, the methods comprise enriching small nucleic acids by methylated DNA immunoprecipitation with an antibody-coated solid support and enriching small nucleic acids by size exclusion. In some embodiments, the methods comprise enriching small nucleic acids by methylated DNA immunoprecipitation with an antibody-coated solid support and enriching small nucleic acids by coefficient of drag alteration sizing. In some embodiments, the methods comprise enriching small nucleic acids by methylated DNA immunoprecipitation with an antibody-coated solid support and enriching small nucleic acids by solid phase reversible immobilization sizing. In some embodiments, the methods comprise enriching small nucleic acids by methylated DNA immunoprecipitation with an antibody-coated solid support and enriching small nucleic acids by electrophoresis-based sizing. In some embodiments, the methods comprise enriching small nucleic acids by methylated DNA immunoprecipitation with an antibody-coated solid support and enriching small nucleic acids by affinity chromatography.

In some embodiments, the methods comprise enriching small nucleic acids by size exclusion and eluting small nucleic acids preferentially from silica. In some embodiments, the methods comprise enriching small nucleic acids by size exclusion and retaining large nucleic acids preferentially on silica. In some embodiments, the methods comprise enriching small nucleic acids by size exclusion and enriching small nucleic acids by methylated DNA immunoprecipitation with an antibody-coated solid support. In some embodiments, the methods comprise enriching small nucleic acids by size exclusion and enriching small nucleic acids by coefficient of drag alteration sizing. In some embodiments, the methods comprise enriching small nucleic acids by size exclusion and enriching small nucleic acids by solid phase reversible immobilization sizing. In some embodiments, the methods comprise enriching small nucleic acids by size exclusion and enriching small nucleic acids by electrophoresis-based sizing. In some embodiments, the methods comprise enriching small nucleic acids by size exclusion and enriching small nucleic acids by affinity chromatography.

In some embodiments, the methods comprise enriching small nucleic acids by coefficient of drag alteration sizing and eluting small nucleic acids preferentially from silica. In some embodiments, the methods comprise enriching small nucleic acids by coefficient of drag alteration sizing and retaining large nucleic acids preferentially on silica. In some embodiments, the methods comprise enriching small nucleic acids by coefficient of drag alteration sizing and enriching small nucleic acids by methylated DNA immunoprecipitation with an antibody-coated solid support. In some embodiments, the methods comprise enriching small nucleic acids by coefficient of drag alteration sizing and enriching small nucleic acids by size exclusion. In some embodiments, the methods comprise enriching small nucleic acids by coefficient of drag alteration sizing and enriching small nucleic acids by solid phase reversible immobilization sizing. In some embodiments, the methods comprise enriching small nucleic acids by coefficient of drag alteration sizing and enriching small nucleic acids by electrophoresis-based sizing. In some embodiments, the methods comprise enriching small nucleic acids by coefficient of drag alteration sizing and enriching small nucleic acids by affinity chromatography.

In some embodiments, the methods comprise enriching small nucleic acids by solid phase reversible immobilization sizing and eluting small nucleic acids preferentially from silica. In some embodiments, the methods comprise enriching small nucleic acids by solid phase reversible immobilization sizing and retaining large nucleic acids preferentially on silica. In some embodiments, the methods comprise enriching small nucleic acids by solid phase reversible immobilization sizing and enriching small nucleic acids by methylated DNA immunoprecipitation with an antibody-coated solid support. In some embodiments, the methods comprise enriching small nucleic acids by solid phase reversible immobilization sizing and enriching small nucleic acids by size exclusion. In some embodiments, the methods comprise enriching small nucleic acids by solid phase reversible immobilization sizing and enriching small nucleic acids by coefficient of drag alteration sizing. In some embodiments, the methods comprise enriching small nucleic acids by solid phase reversible immobilization sizing and enriching small nucleic acids by electrophoresis-based sizing. In some embodiments, the methods comprise enriching small nucleic acids by solid phase reversible immobilization sizing and enriching small nucleic acids by affinity chromatography. In some embodiments, the methods comprise enriching small nucleic acids by electrophoresis-based sizing and eluting small nucleic acids preferentially from silica. In some embodiments, the methods comprise enriching small nucleic acids by electrophoresis-based sizing and retaining large nucleic acids preferentially on silica. In some embodiments, the methods comprise enriching small nucleic acids by electrophoresis-based sizing and enriching small nucleic acids by methylated DNA immunoprecipitation with an antibody-coated solid support. In some embodiments, the methods comprise enriching small nucleic acids by electrophoresis-based sizing and enriching small nucleic acids by size exclusion. In some embodiments, the methods comprise enriching small nucleic acids by electrophoresis-based sizing and enriching small nucleic acids by coefficient of drag alteration sizing. In some embodiments, the methods comprise enriching small nucleic acids by electrophoresis-based sizing and enriching small nucleic acids by solid phase reversible immobilization sizing. In some embodiments, the methods comprise enriching small nucleic acids by electrophoresis-based sizing and enriching small nucleic acids by affinity chromatography.

In some embodiments, the methods comprise enriching small nucleic acids by affinity chromatography and eluting small nucleic acids preferentially from silica. In some embodiments, the methods comprise enriching small nucleic acids by affinity chromatography and retaining large nucleic acids preferentially on silica. In some embodiments, the methods comprise enriching small nucleic acids by affinity chromatography and enriching small nucleic acids by methylated DNA immunoprecipitation with an antibody-coated solid support. In some embodiments, the methods comprise enriching small nucleic acids by affinity chromatography and enriching small nucleic acids by size exclusion. In some embodiments, the methods comprise enriching small nucleic acids by affinity chromatography and enriching small nucleic acids by coefficient of drag alteration sizing. In some embodiments, the methods comprise enriching small nucleic acids by affinity chromatography and enriching small nucleic acids by solid phase reversible immobilization sizing. In some embodiments, the methods comprise enriching small nucleic acids by affinity chromatography and enriching small nucleic acids by electrophoresis-based sizing. In some embodiments, the methods comprise dual and simultaneous anion exchange and size exclusion using amine-functionalized beads having an irregular surface (e.g., comprising micron or sub-micron sized pores).

The methods find use in non-invasive prenatal testing; thus, in some embodiments the input sample is a blood sample (e.g., a blood sample from a pregnant woman) and the methods comprise testing a subject for a chromosomal aberration such as an aneuploidy by PCR or digital counting by sequencing. Some embodiments find use in detecting monogenic fetal disorders and placental-related disorders.

Other embodiments find utility in cancer applications for screening, diagnosis, prognosis, and monitoring residual disease or disease recurrence (e.g., to detect, quantify, and/or characterize a biomarker (e.g., methylated septin 9 (ms9)) for colorectal cancer detection and screening, e.g., as provided by a bisulfite PCR assay (e.g., as provided commercially by the Abbott Molecular mS9 bisulfite PCR assay on the m2000rt real-time PCR platform)). In some embodiments, the technology finds use in detecting, characterizing, and/or quantifying small circulating cell-free nucleic acids (e.g., small circulating cell-free DNA and/or small circulating cell-free RNA) for applications related to testing (e.g., assessing risk (e.g., of acquiring or developing); detecting a presence of, an absence of, a predisposition to develop, or a predisposition not to develop; screening; diagnosis; prognosis; and/or monitoring residual disease or recurrence) associated with a variety of human and non-human, acute and chronic disease state pathologies (pathophysiologies) including, but not limited to: oncology, hematology, infectious disease, liver disease, cardiovascular (e.g., heart) disease, renal disease, inflammatory disease (e.g., rheumatic, arthritic, bronchial, gastrointestinal, dermal, cerebrospinal, etc.), and various forms of pulmonary disease (e.g. emphysema, COPD, mesothelioma).

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 2A shows the size distribution prior to enrichment. FIG. 2B shows the distribution in an output sample after enrichment with a commercial kit designed to isolate free-circulating DNA and RNA from human plasma or serum (Qiagen Circulating Nucleic Acid kit). FIG. 2C shows the distribution in an output sample after enrichment using Beckman AMPure SPRI beads. FIG. 2D shows the distribution in an output sample after enrichment using Abbott Molecular SPRI beads. The amounts of each fragment of the test sample were quantified before and after enrichment using gel electrophoresis and densitometric analysis of gel images. FIG. 2E shows that both the AMPure and the AM SPRI methods provided an enrichment of small fragments (e.g., less than 500 bp, bases, or nt) of approximately 150%.

FIG. 4A shows results of tests of an ethanol wash buffer and FIG. 4B shows results of tests of a wash buffer comprising 10% Tween-20, 15% ethanol, and 20 mM $MgCl_2$.

FIG. 6A shows results using irregular surface contour beads and FIG. 6B shows results from smooth surface contour beads.

Figure 1:
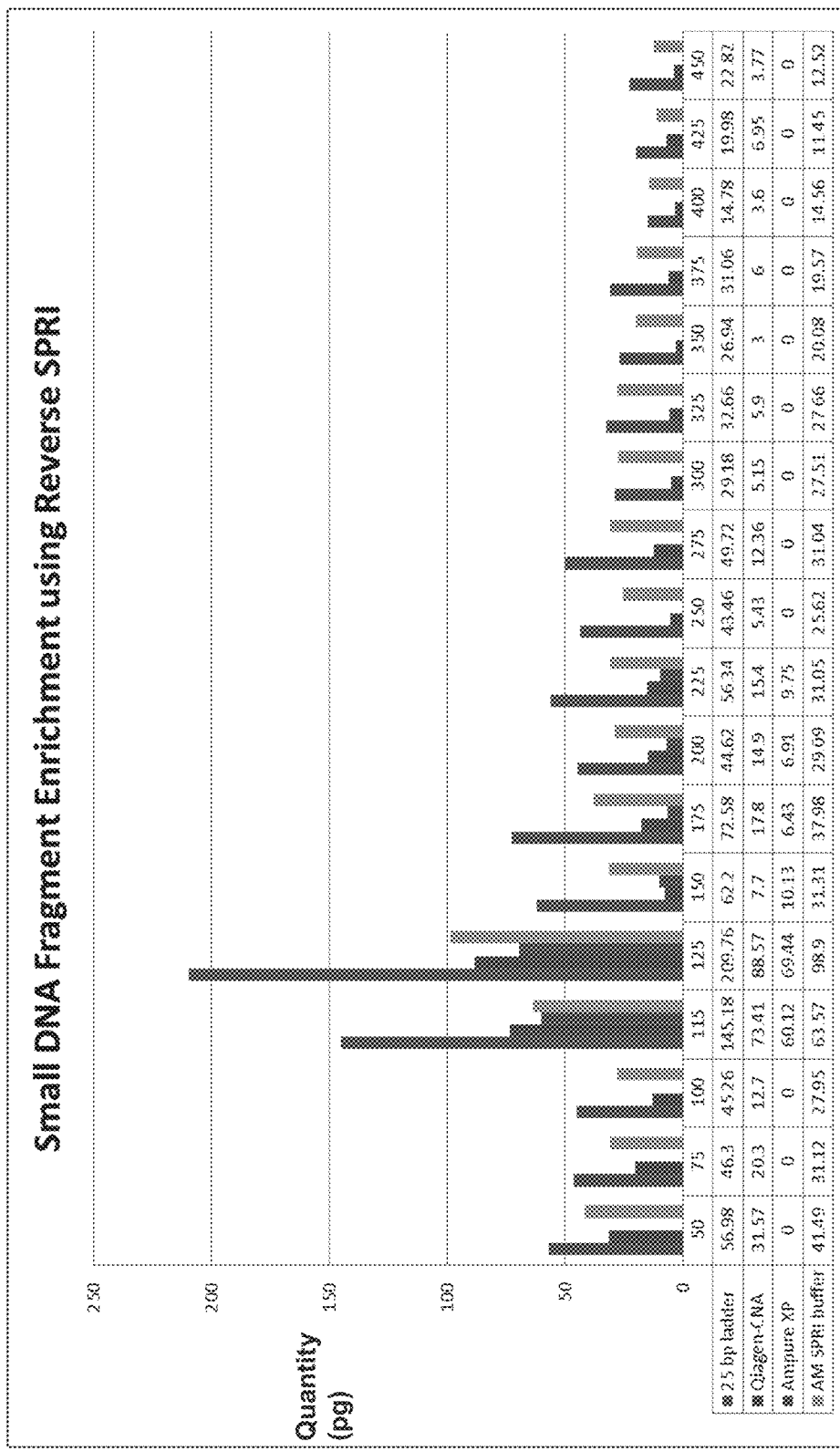
FIG. 1 is a plot showing the enrichment of small nucleic acids using "reverse SPRI" methodology.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology related to processing samples of nucleic acids and particularly, but not exclusively, to methods for enriching samples for small nucleic acids, such as small circulating cell-free DNA that finds use in prenatal testing and in human disease testing. In some embodiments, the technology relates to detecting, characterizing, and/or quantifying small circulating cell-free nucleic acids for cancer-related applications such as screening, diagnosis, prognosis, and monitoring residual disease or disease recurrence. In some embodiments, the technology relates to identifying, characterizing, and/or quantifying small circulating cell-free DNA and/or small circulating cell-free RNA) for applications related to testing (e.g., assessing risk (e.g., of acquiring or developing); detecting a presence of, an absence of, a predisposition to develop, or a predisposition not to develop; screening; diagnosis; prognosis; and/or monitoring residual disease or recurrence) associated with a variety of human and non-human, acute and chronic disease state pathologies (pathophysiologies) including, but not limited to: oncology, hematology, infectious disease, liver disease, cardiovascular (e.g., heart) disease, renal disease, inflammatory disease (e.g., rheumatic, arthritic, bronchial, gastrointestinal, dermal, cerebrospinal, etc.), and various forms of pulmonary disease (e.g. emphysema, COPD, mesothelioma).

In this description of various embodiments of the technology, the section headings used herein are for organizational purposes only and are not to be construed as limiting the described subject matter in any way. In addition, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings interpreted consistently with the understanding of one of ordinary skill in the related art as explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the term "SPRI" refers to the technology of "Solid Phase Reversible Immobilization" wherein target nucleic acids are selectively precipitated under specific buffer conditions in the presence of beads or other solid phase materials that are often carboxylated and paramagnetic. The precipitated target nucleic acids immobilize to said beads and remain bound until removed by an elution buffer according to the operator's needs (see, e.g., DeAngelis et al. (1995) *Nucleic Acids Res* 23: 4742-4743). The term "carboxylated" as used herein refers to the modification of a material, such as a microparticle, by the addition of at least one carboxyl group (e.g., COOH or COO—). In some embodiments, SPRI is used to bind nucleic acids of interest to the solid phase and in some embodiments SPRI is used to bind and retain nucleic acids that are not of interest, e.g., the nucleic acids of interest remain in the non-bound liquid phase (e.g., "reverse SPRI").

As used herein, the term "paramagnetic" as used herein refers to the characteristic of a material wherein said material's magnetism occurs only in the presence of an external, applied magnetic field and does not retain any of the magnetization once the external, applied magnetic field is removed.

As used herein, the term "bead" refers to any type of solid phase particle of any convenient size, of irregular or regular shape, and which is fabricated from any number of known materials such as cellulose, cellulose derivatives, acrylic resins, glass, silica gels, polystyrene, gelatin, polyvinyl pyrrolidone, co-polymers of vinyl and acrylamide, polystyrene cross-linked with divinylbenzene, or the like (as described, e.g., in Merrifield (1964) *Biochemistry* 3: 1385-1390), polyacrylamides, latex gels, polystyrene, dextran, rubber, silicon, plastics, nitrocellulose, natural sponges, silica gels, controlled pore glass (CPG), metals, cross-linked dextrans (e.g., Sephadex™), agarose gel (Sepharose™), and other solid phase bead supports known to those of skill in the art.

"Support", as used herein, refers to a matrix on or in which nucleic acid molecules, microparticles, and the like may be immobilized, e.g., to which they may be covalently or noncovalently attached or in or on which they may be partially or completely embedded so that they are largely or entirely prevented from diffusing freely or moving with respect to one another.

As used herein, the terms "chromosomal abnormality", "chromosomal aberration", and "chromosomal alteration" are used herein interchangeably. They refer to a difference (e.g., a variation) in the number of chromosomes or to a difference (e.g., a modification) in the structural organization of one or more chromosomes as compared to chromosomal number and structural organization in a karyotypically normal individual. As used herein, these terms are also meant to encompass abnormalities taking place at the gene level. Examples of aneuploidy are trisomy 21 and trisomy 13. In some contexts, the terms "chromosomal abnormality" and "chromosomal aberration" are used interchangeably to refer to numerical and structural alterations in a chromosome that give rise to an abnormal or pathological phenotype. Chromosomal abnormalities can be of several types, for example, extra or missing individual chromosomes, extra or missing portions of a chromosome (segmental duplications or deletions), breaks, rings and rearrangements, among others.

As used herein, a "copy-number variation" ("CNV") refers to an alteration of DNA (e.g., in a genome) that results in a cell having an abnormal number of copies of one or more sections of the DNA. Typically, CNVs correspond to relatively large regions of a genome that have been deleted (e.g., the genome comprises fewer than the normal number) or duplicated (e.g., the genome comprises more than the normal number) on certain chromosomes. For example, a chromosome that normally has sections in order as L-M-N-O might instead have sections L-M-N-N-O (e.g., a duplication of N) or L-M-O (e.g., a deletion of N). CNV can also result from aneuploidy and insertion events. In humans, CNV accounts for roughly 12% of human genomic DNA and each variation typically ranges from hundreds or thousands of bases (e.g., from approximately one kilobase (1000 nucleotide bases)) to several megabases in size.

The presence of an abnormal number of (e.g., either too many or too few) chromosomes or chromosome fragments is called "aneuploidy", e.g., the occurrence of at least one more or one less chromosome than the normal diploid number of chromosomes leading to an unbalanced chromosome complement. Chromosomal aneuploidy is associated with a large number of genetic disorders and degenerative diseases. While many examples are provided herein of aneuploidies comprising an abnormally high number of chromosomes, the technology is equally applicable to aneuploidies comprising an abnormally low number of chromosomes. In particular, in descriptions of the technology for discriminating more than 2 (e.g., 3 or more) chromosomes in an aneuploid state versus 2 chromosomes in a euploid state, the technology is to be understood as applicable also to detecting fewer than 2 chromosomes in an aneuploid state (e.g., 1 or 0 chromosomes).

As used herein, the term "disease or condition associated with a chromosomal abnormality" refers to any disease, disorder, condition, or defect that is known or suspected to be caused by a chromosomal abnormality. Exemplary diseases or conditions associated with a chromosomal abnormality include, but are not limited to, trisomies (e.g., Down syndrome (trisomy 21), Edward syndrome (trisomy 18), Patau syndrome (trisomy 13), Kleinfelter syndrome (XXY), triple X syndrome (XXX), and XYY disease), Turner syndrome (absence of X chromosome, e.g., XO), and X-linked disorders (e.g., Duchenne muscular dystrophy, hemophilia A, certain forms of severe combined immunodeficiency, Lesch-Nyhan syndrome, and Fragile X syndrome). Additional examples of diseases or conditions associated with chromosomal abnormalities are described in *Harrison's Principles of Internal Medicine*, Wilson et al. (ed.), 1991 (12th ed.), Mc Graw Hill, New York, N.Y., pp. 24-46, which is incorporated herein by reference in its entirety.

As used herein, a "nucleic acid" refers to a DNA, an RNA, modified DNA, modified RNA, and the like. A nucleic may comprise any number of nucleotides, e.g., from 2 to over a million nucleotides.

The term "sample of DNA" or "DNA sample" refers to a sample comprising DNA or nucleic acid representative of DNA isolated from a natural source and in a form suitable for evaluation by an assay (e.g., as a soluble aqueous solution).

As used herein, the terms "small DNA", "small RNA", "small RNA fragment", "small DNA fragment", "small nucleic acid", etc., refer to a nucleic acid (e.g., a DNA or an RNA) (e.g., a collection of individual nucleic acids in a sample) that is smaller than a "cutoff" value. In exemplary embodiments, small nucleic acid refers to a nucleic acid that has a size smaller than 1000, 900, 800, 700, 600, 500, 400, 300, 275, 250, 225, 200, 175, 150, 125, 100, 75, or 50 base pairs (bp), bases, or nucleotides (nt); preferably, the small nucleic acid is from approximately 50 to approximately 500 base pairs, bases, or nucleotides or from approximately 50 to approximately 400 base pairs, bases, or nucleotides, or from approximately 50 to approximately 300 base pairs, bases, or nucleotides or from approximately 50 to approximately 200 base pairs, bases, or nucleotides or from approximately 50 to approximately 100 base pairs, bases, or nucleotides. As used herein, a "large DNA", "large RNA", "large RNA fragment", "large DNA fragment", "large nucleic acid", etc., refer to a nucleic acid (e.g., a DNA or an RNA) (e.g., a collection of individual nucleic acids in a sample) that is larger than the cutoff value.

Size may be defined by mass, length, or other suitable size measures. The length of a nucleic acid may be expressed in units indicating as a number of "base pairs" (abbreviated "bp"), a number of "bases", or a number of nucleotides ("nt" or "nts"). Lengths of double stranded nucleic acids (e.g., DNA) are typically, but not exclusively, expressed in units of base pairs (bp). Lengths of single stranded nucleic acids (e.g., DNA) are typically, but not exclusively, expressed in units of nucleotides (nt). Lengths expressed in units of bases may apply to either double stranded nucleic acids or single stranded nucleic acids. These units are modifiable with standard SI prefixes to indicate multiples of powers of 10, e.g., kbp, Mbp, Gbp, kilobase, Megabase, Gigabase, etc.), The size measurement can be performed in various ways known in the art, e.g., paired-end sequencing and alignment of nucleic acids, electrophoresis, centrifugation, optical methods, mass spectrometry, etc. A statistically significant number of nucleic acids can be measured to provide an accurate size profile of a sample. In some embodiments, the data obtained from a physical measurement is received at a computer and analyzed to accomplish the measurement of the sizes of the nucleic acids. For example, the electropherogram resulting from electrophoresis can be analyzed (e.g., by densitometric analysis of electropherogram bands, peaks, etc.) to determine the sizes. In one implementation, analyzing the nucleic acids does include the actual process of sequencing or subjecting nucleic acids to electrophoresis, while other implementations perform an analysis of the resulting data. In some embodiments, a parameter provides a statistical measure of the size distribution (e.g., a histogram) of nucleic acids in the biological sample. The parameter may be referred to as a size parameter since it is determined from the sizes of the plurality of nucleic acids.

By "maternal host of a fetus" is meant a woman who is pregnant with a fetus whose DNA is sought to be detected and/or tested for a genetic condition. The term "maternal host of a fetus", "maternal host", and "mother" are used interchangeably. By "fetus" is meant an offspring developing in utero at any gestational stage. Fetal DNA can be detected prior to the "fetal period" which begins at 10 or 11 weeks of gestation in a human. Therefore, "fetus" encompasses not only the developing offspring in the fetal period but also in the earlier embryonic stages of development prior to the 10th or 11th week of human gestation.

A "subject" is a vertebrate, preferably a mammal, more preferably a human. Mammals include, but are not limited to, murines, simians, humans, farm animals, sport animals, and pets.

As used herein, "cell-free DNA" refers to DNA that is not within a cell. In one embodiment, cell free DNA includes DNA circulating in blood. In another embodiment, cell free DNA includes DNA existing outside of a cell. In yet another embodiment, cell free DNA includes DNA existing outside of a cell as well as DNA present in a blood sample after such blood sample has undergone partial or gentle cell lysing.

As used herein, "cell-free fetal DNA" ("cffDNA") refers to DNA that originated from the fetus and not the mother and is not within a cell. In one embodiment, cell free fetal DNA includes fetal DNA circulating in maternal blood. In another embodiment, cell free fetal DNA includes fetal DNA existing outside of a cell, for example a fetal cell. In yet another embodiment, cell free fetal DNA includes fetal DNA existing outside of a cell as well as fetal DNA present in maternal blood sample after such blood sample has undergone partial or gentle cell lysing. A review of fetal DNA in maternal plasma and serum is provided by Peril and Bianchi (2001), as well as in Lo (2000).

By "biological sample" is meant any sample that is derived from the maternal host of the fetus. In one embodiment, the biological sample of a maternal host includes any processed or unprocessed, solid, semi-solid, or liquid biological sample, e.g., blood, urine, saliva, and mucosal samples (e.g., samples from uterus or vagina, etc.). For example, the biological sample of a maternal host can be a sample of whole blood, partially lysed whole blood, plasma, and/or partially processed whole blood. In one embodiment, the biological sample of a maternal host is a sample of cell free DNA or free floating DNA from the whole blood of the maternal host.

As used herein, the term "Tween-20" refers to a polysorbate surfactant, e.g., a polyoxyethylene derivative of sorbitan monolaurate (e.g., Polysorbate 20 (polyoxyethylene (20) sorbitan monolaurate)). Tween-20 is distinguished from other members in the polysorbate range by the length of the polyoxyethylene chain and the fatty acid ester moiety. Accordingly, other Tween surfactants are Tween-40 (Polysorbate 40 (polyoxyethylene (20) sorbitan monopalmitate)), Tween-60 (Polysorbate 60 (polyoxyethylene (20) sorbitan monostearate)), Tween-80 (Polysorbate 80 (polyoxyethylene (20) sorbitan monooleate)), etc. The number 20 following "polyoxyethylene" refers to the total number of oxyethylene —$(CH_2CH_2O)$— groups found in the molecule. The number following "polysorbate" is related to the type of fatty acid associated with the polyoxyethylene sorbitan part of the molecule. Monolaurate is indicated by 20, monopalmitate is indicated by 40, monostearate by 60, and monooleate by 80. In some embodiments where Tween-20 is described another detergent or surfactant can be substituted, e.g., a Tween-40, a Tween-60, and/or a Tween-80.

Description

The technology provides a variety of approaches to use alone or in combination to enrich low-abundance nucleic acids (e.g., DNA and/or RNA such as small circulating fetal DNA fragments, mRNA, miRNA, piRNA, etc.) from the abundant background of circulating maternal nucleic acids (e.g., DNA and/or RNA) present in maternal plasma specimens. In some embodiments, the technology is applicable to the selective enrichment of small nucleic acids (e.g., having a length of less than approximately 200 bp, bases, or nt) from a background milieu of larger molecular weight nucleic acids (e.g., having a length of greater than approximately 200 bp, bases, or nt and extending up to approximately 20,000 or more bp, bases, or nt). The technology is not limited in the size cutoff (e.g., in bp, bases, or nt) that is used to differentiate "small" from "large" or "non-small" nucleic acids. As used herein, reference to a 200-bp, 200-base, or 200-nt cut-off to differentiate between small nucleic acids and large nucleic acids in size distributions is intended to be exemplary and is not intended to limit the technology to that particular size cut-off. Accordingly, in some embodiments a size cut-off of 200 bp, bases, or nt is used to differentiate small nucleic acids (e.g., DNA (e.g., cffDNA) and/or RNA) from large nucleic acids (e.g., maternal nucleic acids). In some embodiments, cut-off values of, e.g., 1000, 900, 800, 700, 600, 500, 400, 300, 275, 250, 225, 200, 175, 150, 125, 100, 75, or 50 base pairs, bases, or nucleotides are used. Desirable cut-off values can be determined by one of skill in art for particular applications.

In addition, the technology provided does not introduce detectable or otherwise discernible genome and/or sequence representational bias other than size discrimination that could have the potential to compromise downstream sensitivity in aneuploid marker analyses for non-invasive prenatal testing (NIPT) applications.

The technology is not limited in the type of nucleic acid that is enriched. Accordingly, the technology is applicable to the isolation, enrichment, and detection of DNA (e.g., cffDNA and other small DNA and DNA fragments). The technology is applicable to the isolation, enrichment, and detection of RNA, such as messenger RNAs (mRNA), micro RNAs (microRNA or miRNA), piRNA, and other small nucleic acids (e.g., nucleic acids present in blood) as well as for the isolation, enrichment, and detection of fetal messenger RNAs (mRNA) and fetal micro RNAs (microRNA or miRNA) present in maternal blood.

The technology is exemplified herein by two general types of strategies and sub-technologies. However, it is understood that the technology is not limited to these illustrative examples. The first set of sub-technologies provides a selective and preferential (e.g., enriched) elution of small nucleic acids directly from silica-based capture membranes and matrices (e.g., the Qiagen Circulating Nucleic Acid Kit or the Qiagen DNeasy kit). The second set of sub-technologies relies on secondary enrichment processes that require additional laboratory instrumentation such as methylated DNA immunoprecipitation (e.g., "MeDIP") with antibody-coated particles that can be captured with a magnetic field (e.g., antibody-coated paramagnetic particles or antibody-coated magnetic particles)) or capture onto affinity columns (e.g., antibody-coated spin-columns, e.g., as provided commercially by Molzyme) or other solid supports (e.g., microtiter plates, beads, slides, or nanostructures), solid phase reversible immobilization (SPRI) beads, automated electrophoresis and electroelution (e.g., life technologies Pippin Prep), LabChip XT, synchronous coefficient drag of alteration (SCODA), simultaneous anion exchange and size exclusion, etc. These methods can either be used directly and independently to isolate small nucleic acids from plasma (e.g., to provide a single-enrichment method) and/or sequentially on the back-end of a silica membrane capture process (e.g., to provide a double-enrichment method, e.g., used in conjunction with a silica-based isolating method such as a Qiagen Circulating Nucleic Acid Kit, which is modified in some embodiments according to the technology provided herein). Although the disclosure herein refers to certain illustrated embodiments, it is to be understood that these embodiments are presented by way of example and not by way of limitation.

1. Preferential Elution of Small Nucleic Acids from Silica

In some embodiments of the technology, small nucleic acids (e.g., small DNA (e.g., cffDNAs) and/or small RNA) are isolated from or enriched in a sample (e.g., a sample prepared or derived from maternal blood or plasma) by preferential and/or selective elution. For example, in some embodiments small nucleic acids are preferentially eluted or otherwise recovered from a silica matrix or membrane after capture (e.g., binding) of bulk or total nucleic acid from the sample on the silica matrix or membrane.

Nucleic acids (e.g., DNA, RNA) bind non-specifically to silica surfaces in the presence of certain salts and under certain pH conditions, usually under conditions of high ionic strength. For example, DNA adsorption is most efficient in the presence of a buffer solution having a pH at or below the pKa of the surface silanol groups of the silicon surface. In some embodiments, a nucleic acid (e.g., DNA) binds to silica in the presence of a chaotrope (e.g., salts, butanol, ethanol, guanidinium chloride, guanidine thiocyanate, lithium perchlorate, lithium acetate, magnesium chloride, phenol, propanol, sodium dodecyl sulfate, thiourea, and urea), which denatures biomolecules by disrupting the shell of hydration around them. In some embodiments, the nucleic acid is washed with high salt and ethanol, and typically eluted with an elution buffer comprising low salt.

Accordingly, in some embodiments, after binding of total or bulk nucleic acids (e.g., from a maternal blood sample), elution conditions promote the selective and preferential release of small nucleic acids from the silica surface relative to large nucleic acids. In exemplary embodiments, solvent effects act to promote the elution of small nucleic acids from silica. Accordingly, embodiments provide for the preferential elution of small nucleic acids from silica in an elution buffer comprising 5 to 25% ethanol, 5 to 25% methanol, 5 to 25% acetonitrile, 5 to 25% DMSO, and/or 1 to 25% formamide. In some embodiments, ionic strength effects act to promote the preferential elution of small nucleic acids from silicon. Accordingly, embodiments provide for the preferential elution of small nucleic acids from silica in an elution buffer comprising an elevated sodium chloride concentration (e.g., greater than 500 mM, e.g., 1 M or higher) to screen counter-ion binding interactions and/or comprising an elevated chaotropic salt concentration to stabilize binding of larger nucleic acids to the silica surface. In some embodiments, pH effects preferentially promote the elution of small nucleic acids from silica membranes or columns. In some embodiments, elution conditions are adjusted to modify the kinetics of adsorption and release from the silica to favor the release of small nucleic acids from the silica, e.g., at low temperatures (e.g., 2° C. to 16° C.) small nucleic acids are preferentially eluted from a silica column.

2. Preferential Retention of Large Nucleic Acids on Silica

Furthermore, in some embodiments of the technology, small nucleic acids (e.g., DNA (e.g., cffDNAs) and/or small RNA) are isolated from or enriched in a sample (e.g., a sample prepared or derived from maternal blood or plasma) by selective and preferential retention of large nucleic acids by post-capture silica column sequestration. In some embodiments, after binding of total or bulk nucleic acids (e.g., from a maternal blood sample), elution conditions promote the selective and preferential retention of large nucleic acids by the silica surface relative to small nucleic acids.

For example, in some embodiments a silica surface (membrane, column, etc.) is treated with a polymer coating, volume-exclusion agent, or absorptive agent to sequester large nucleic acids (e.g., greater than 200 bp, bases, or nt) onto the column and promote the elution of small nucleic acids (e.g., less than 200 bp, bases, or nt). Exemplary embodiments provide a method in which nucleic acids (e.g., DNA) are adsorbed to a silica surface treated with 0.5 to 2% acrylamide/bis-acrylamide (e.g., comprising a 19:1 to 29:1 cross-linking ratio), 0.01 to 0.5% agarose, 0.01 to 1.0% polyethylene glycol (PEG having an average molecular weight of 1000 to 10,000), 1 to 10% dextran sulfate, 1 to 10% ficoll, sorbitol, or sugar (e.g., aldohexose) polymer, 1 to 10% polyvinyl alcohol (PVA), 1 to 10% polyamines (e.g., spermine, spermidine, etc.), or a low-level synthetic polymer such as, e.g., nylon, polyester, polystyrene, etc.

In some embodiments, a doped silica membrane and/or column matrix sequesters large nucleic acids (e.g., greater than 200 bp, bases, or nt) onto the column and promotes the elution of small nucleic acids (e.g., less than 200 bp, bases, or nt) from the column. For example, some embodiments comprise the use of silica embedded with an amine-binding surface doping agent (e.g., carboxylate group derivatization). In some embodiments, silica is embedded with a polyphosphate-binding surface doping agent (e.g., amino group derivatization). In some embodiments, silica is embedded with one or more of a reversible, controllable, or amine-reactive surface group for the controlled, reversible, and preferential elution of small nucleic acids. In some embodiments, silica is embedded with one or more of a reversible, controllable, or carboxyl-reactive surface group for the controlled, reversible, or preferential elution of small nucleic acids.

In some embodiments, the technology provides methods comprising preferential cross-linking of large nucleic acids relative to small nucleic acids to retain the large nucleic acids on a substrate (e.g., a silica column). For example, in some embodiments methods comprise low-level ultraviolet radiation cross-linking of large nucleic acids, e.g., at low energy intensities to entrap large cross-linked molecular weight nucleic acids, e.g., greater than 200 bp, bases, or nt. In some embodiments, methods comprise endogenous cross-linking of nucleic acids, e.g., to from cyclobutane and/or thymidine dimers preferentially in large nucleic acids (e.g., DNA) relative to small nucleic acids. In some embodiments, methods comprise cross-linking large nucleic acids preferentially using ultraviolet radiation in the presence of an exogenous cross-linking agent such as, e.g., psoralen.

In some embodiments, methods comprise the use of low-level chemical cross-linking (e.g., to promote the reversible, controlled, and preferential elution of small size nucleic acids). For example, some embodiments provide a method comprising preferentially cross-linking large nucleic acids using a solution comprising 10% neutral, buffered formalin. Formalin treatment is followed, in some embodiments, by heat restoration with or without treatment with EDBE (e.g., the Gundling reagent for preparing formalin-fixed paraffin embedded samples; see, e.g., U.S. Pat. Appl. Pub. No. 20130323815, incorporated herein by reference).

In some embodiments, methods comprise use of a reversible, bi-functional cross-linking agent (e.g. a DTT-cleavable, thiol-labile bis-acrylamide/acrylamide mixture). In embodiments associated with testing maternal blood for fetal nucleic acids, these low-level cross-linking methods exploit the lower abundance of smaller (e.g., fetal) nucleic acids (e.g., DNA) relative to longer (e.g., maternal) nucleic acids. Without being bound by theory, it is expected both statistically and stochastically that larger (e.g., maternal) nucleic acid molecules will be preferentially cross-linked to one another compared to the less abundant smaller (e.g., fetal) nucleic acids. This effect is further enhanced by the relative lengths of the large and small nucleic acid molecules because larger species are more likely to be cross-linked by both intra-strand and inter-strand cross-linking events. Some embodiments comprise use of a cross-linking agent comprising formalin, alkylating agents (e.g., 1,3-bis(2-chloroethyl)-1-nitrosourea (BCNU, carmustine)), nitrogen mustard, cisplatin, nitrous acid, aldehydes (e.g., malondialdehyde, acrolein, crotonaldehyde), chloroethylating agents, nitrosoureas, triazenes, alkyl sulfonates, epoxides, diepoxybutane, carzinophilin, azinomycin B, cis-Diamminedichloroplatinum (II), sandramycin, luzopeptins, isochrysohermidin, pyrrolobenzodiazepine agents, cyclophosphamide, N,N,N,N',N',N'-hexamethylmelamines, pyrrolizidine alkaloids, anthracyclines, mitomycin C, aziridinylbenzoquinones, or biselezin.

Some embodiments provide electroelution methods. For instance, some embodiments provide methods comprising the preferential electroelution of small nucleic acids from a column. Some embodiments comprise continuous forward-field electro-elution (e.g., low-field, cathode assisted electro-elution), continuous reverse-field electro-elution (e.g., low-field, anode assisted electro-elution), or oscillating-field electro-elution (e.g., high frequency, low-field, reversible anode/cathode electrical oscillation-driven electro-elution).

Some embodiments provide methods comprising use of an ion-exchange column with selective elution of small nucleic acids. Examples of column, matrix, or membrane media include but are not limited to silica, DEAE, Dionex, or other derivatized chromatography column media, matrix, or membrane. Some embodiments comprise elution (e.g., isocratic and/or non-isocratic elution) with increasing or decreasing salt gradient, elution (e.g., isocratic and/or non-isocratic elution) with increasing or decreasing pH gradient, and/or elution (e.g., isocratic and/or non-isocratic elution) with an aqueous/non-aqueous (e.g. methanol, ethanol, acetonitrile) dual-solvent, gradient elution system.

3. Preferential Retention of Large Nucleic Acids During Column Washing

In related embodiments of methods, large nucleic acids are retained on a solid support (e.g., a silica column) and/or small nucleic acids are not retained on the solid support during a washing step (e.g., prior to an elution step). For example, in some embodiments, a sample comprising nucleic acids is flowed over a column to bind nucleic acids to the column. Then, the column (comprising bound nucleic acids) is washed with a wash buffer. After washing the column with the wash buffer, some nucleic acids remain adsorbed to the column (e.g., preferential adsorption of large nucleic acids to the column; e.g., enrichment of large nucleic acids on the column) and some nucleic acids are removed from the column and are present in the wash buffer (e.g., preferential removal of small nucleic acids from the column in the wash buffer; e.g., enrichment of small nucleic acids in the wash buffer). Thus, in some embodiments, the wash buffer preferentially removes small nucleic acids from the column (e.g., large nucleic acids remain adsorbed to the column). Subsequently, an elution buffer is flowed over the column to remove nucleic acids from the column that remained bound during the wash. The preferential binding of nucleic acids (e.g., large nucleic acids) to the column during the wash step will produce an eluate enriched for large nucleic acids and a wash buffer enriched for small nucleic acids. Thus, an increase of recovery of large nucleic acids in the eluate indicates that the wash buffer flow-through was enriched for small nucleic acids.

In some embodiments, the ratio of wash buffer to sample volume is controlled to stabilize binding of large nucleic acids to the silica during the wash step, which allows smaller nucleic acids to be recovered in the wash buffer (e.g., prior to eluting the large nucleic acids in the elution buffer). In some embodiments, the wash buffer volume to sample buffer volume is 0.7 to 1, 0.6 to 1, 0.5 to 1, 0.4 to 1, 0.3 to 1. Further, in some embodiments the wash buffer comprises ethanol (e.g., 50-60% ethanol (e.g., 70% ethanol)). In some embodiments, the wash buffer comprises Tween-20, ethanol, and $MgCl_2$ (e.g., in some embodiments the wash buffer comprises 10% Tween-20, 15% ethanol, and 20 mM $MgCl_2$). In some embodiments, 70% ethanol is used at a ratio of 0.5:1, 0.4:1, or 0.3:1; in some embodiments, a buffer comprising Tween-20, ethanol, and $MgCl_2$ is used at a ratio of 0.5:1 or 0.4 to 1.

4. Enrichment by Methylated DNA Immunoprecipitation (MeDIP)

Some embodiments of the technology comprise the use of a silica column that has affinity for nucleic acids (e.g., a DNA-binding column, e.g., as provided commercially in the Qiagen Circulating Nucleic Acid kit) coupled with use of methylated DNA immunoprecipitation ("MeDIP") with antibody-coated particles that can be captured with a magnetic field (e.g., antibody-coated paramagnetic particles or antibody-coated magnetic particles)). In particular, methods comprising use of MeDIP comprise incubating the eluate from a silica-based isolation method (e.g., the eluate from a Qiagen Circulating Nucleic Acid kit) with beads functionalized with an antibody recognizing methylated DNA (e.g., antibody-coated particles that can be captured with a magnetic field (e.g., antibody-coated paramagnetic particles or antibody-coated magnetic particles)). In particular, antibodies recognizing the 5-methycytosine moieties on methylated DNA selectively capture the fetal DNA in maternal blood due to the hypermethylation of fetal DNA relative to maternal DNA. Then, in some embodiments, methods further comprise the elution of hypermethylated fetal DNA from a silica column, e.g., by eluting in the presence of excess 5-methylcytosine to provide competitive binding, using heat denaturation and/or inactivation of anti-methylated DNA antibody, using chemical antibody denaturation and/or inactivation (e.g., using formamide, a chaotropic agent, pH, detergents, surfactants, or ionic liquids), or using a physical denaturation process (e.g., sonication (e.g., in the KHz range), ultrasonication (e.g., in the MHz range), bead-beating and/or mechanical agitation (e.g., using a vortexer or other device such as an Eppendorf EpiMotion), e.g., in the presence of solvents and/or adjuvants). Some embodiments further comprise purifying the enriched fetal nucleic acid fraction (e.g., using a bead-based or column-based method such as some PCR cleanup methods) and/or comprise low-level, whole genome amplification (WGA) by random priming with Klenow fragment and dNTPs (e.g., as provided commercially in the Invitrogen BioPrime Random Priming Kit). In some embodiments, methods comprising use of a silica column (e.g., a DNA-binding column) and MeDIP provide approximately 50-fold to 100-fold amplification of cffDNA from the random priming amplification reaction and an expected yield of approximately 2 μg to 5 μg of random primed and amplified fetal DNA without introducing sequence amplification bias (e.g., resulting in unbalanced marker coverage) or bias in genome representation.

5. Enrichment by Size Exclusion

In some embodiments, the technology provides embodiments of methods in which silica capture is coupled with size exclusion, chromatography, and/or microdialysis methods. For example, in some embodiments, methods comprise use of ultrafiltration, e.g., in particular, the use of centrifugal sample concentrators (e.g., Amicon, CentriCon) that enrich small nucleic acids (e.g., DNA and/or RNA) by molecular weight-based size-exclusion cut-offs (e.g., molecular weight cutoff ranging from approximately 10,000 to 30,000 Daltons). Thus, in some embodiments, small nucleic acids (e.g., fetal DNA, other small DNA, and/or small RNA) are present in the column flow-through. In some embodiments, methods comprise use of size-exclusion chromatography spin-columns (e.g., G-25, G-50, G-100, etc.) wherein the small nucleic acids are retained in the porous chromatography media and are not present in the high-molecular weight flow-through, which represents the column void-volume. In some embodiments, methods comprise microdialysis of fetal nucleic acids followed by diluent-exchange buffer recovery and concentration of low-molecular weight nucleic acid in a sample. In particular, in some embodiments methods employ use of a dialysis membrane with a nominal molecular weight cutoff range of approximately 10,000 to 30,000 Daltons followed by either silica membrane re-capture, rotary-vapor exchange buffer concentration, vacuum concentration (e.g., by a Speed-Vac brand vacuum concentrator or equivalent), centrifugal evaporation (e.g., by a Speed-Vac brand vacuum concentrator or equivalent), and/or ethanol precipitation to capture the permeate from the microdialysis filtration exchange buffer.

6. Synchronous Coefficient of Drag Alteration (SCODA) Sizing

In some embodiments, small nucleic acids are enriched, isolated, or obtained from a sample using a method comprising separation by synchronous coefficient of drag alteration (SCODA), e.g., as implemented in a commercial product such as the Aurora system by Boreal Genomics (Vancouver, BC). The method is based on the non-linear response of nucleic acids (e.g., DNA and/or RNA) to electrophoretic fields that causes them to drift relative to other components under certain types of superimposed, rotating electric fields. See, e.g., Pel, et al. (2009) "Nonlinear electrophoretic response yields a unique parameter for separation of biomolecules" *Proc. Nat. Acad. Sci U.S.A.* 106(35): 14796.

7. Solid Phase Reversible Immobilization (SPRI) Bead-Based Sizing

In some embodiments, small nucleic acids are enriched, isolated, or obtained from a sample using a method comprising solid phase reversible immobilization (SPRI), e.g., on a solid support, e.g., beads. See, e.g., DeAngelis et al. (1995) "Solid-phase reversible immobilization for the isolation of PCR products" *Nucleic Acids Res.* 23(22)4742. SPRI beads comprise a paramagnetic magnetite layer between a polystyrene core surrounded and an external polymer surface coated with carboxylate groups. Carboxylate groups reversibly bind nucleic acids (e.g., DNA and/or RNA) in the presence of a crowding agent (e.g., polyethylene glycol (PEG), e.g., at 20% weight per volume) and salt (e.g., 2.5 M NaCl). The crowding agent promotes nucleic acids to bind with the carboxyl groups on the bead surface.

The PEG concentration and/or ratio of beads to total nucleic acids are adjusted for size selection, e.g., to enrich a sample for small nucleic acids. As PEG concentration and bead-to-nucleic acid ratio vary, the length of fragments binding and/or left in solution changes. In general, the higher the concentrations of PEG and salt in the solution, the lower the cutoff size. While fragments larger than the cutoff (e.g., based on the solution conditions, e.g., PEG and/or salt concentrations) are bound to the beads and thus are removed from the sample, fragments smaller than the cutoff are retained in the buffer. In some contexts, the term "reverse SPRI" refers to the use of SPRI beads to recover small nucleic acids in the buffer rather than the long nucleic acids bound to the beads. Some exemplary commercial products comprising SPRI technology are, e.g., Ampure XP beads from Beckman.

The technology is adaptable to a range of cutoff values for differentiating small DNA from large DNA. For example, PEG concentration can be adjusted to provide for the desired cutoff (e.g., using PEG (e.g., PEG 8000) concentrations of 4 to 5%, e.g., 4.0%, 4.1%, 4.2%, 4.3%, 4.4%, 4.5%, 4.6%, 4.7%, 4.8%, 4.9%, or 5.0%). Accordingly, embodiments provide methods for enriching a sample for small DNA, wherein small DNA is DNA having a length less than a length cutoff value of 1000, 900, 800, 700, 600, 500, 400, 300, 275, 250, 225, 200, 175, 150, 125, 100, 75, or 50 base pairs, bases, or nucleotides. In some embodiments, the distribution and relative abundance of fragment sizes smaller than a length cutoff value in the output sample and the distribution and relative abundance of fragment sizes of fragment sizes smaller than a length cutoff value in the input sample are the same or similar. In some embodiments, a higher concentration of PEG (e.g., PEG 8000) is used, e.g., 15% to 20% (e.g., 15%, 16%, 17%, 18%, 19%, or 20%).

In some embodiments, the PEG (e.g., PEG 8000) concentration modulates the recovery of smaller (e.g., lower molecular weight) DNA (FIG. 3) relative to larger DNA. For example, a concentration of 5.1% PEG produced a cutoff for recovery at about 600 bp, bases, or nt—e.g., nucleic acids larger than 600 bp, bases, or nt were bound to beads and removed from the sample; nucleic acids smaller than 600 bp, bases, or nt remained in the sample, which was then enriched for small nucleic acids less than 600 bp, bases, or nt. In addition, a concentration of 4.8% PEG produced a cutoff for recovery at about 1000 bp, bases, or nt—e.g., nucleic acids larger than 1000 bp, bases, or nt were bound to beads and removed from the sample; nucleic acids smaller than 1000 bp, bases, or nt remained in the sample, which was then enriched for small nucleic acids less than 1000 bp, bases, or nt.

In some embodiments, SPRI beads find use in manual size fractionation comprising pipetting, mixing, centrifuging, and transferring steps; and, in some embodiments, SPRI beads find use in automated SPRI size fractionation, e.g., using Beckman Coulter Genomics SPRI-TE NGS robotics, which is adaptable to many instruments for sample preparation such as those available from Precision System Science. In some embodiments, methods comprise steps to determine the ionic strength (e.g., NaCl concentration) and PEG concentration for the desired cutoff (e.g., between the appropriate small fragments and large fragments) for a size-specific nucleic acid precipitation on SPRI bead surfaces.

8. Electrophoresis-Based Sizing

In some embodiments, small nucleic acids are enriched, isolated, or obtained from a sample using a method comprising electrophoresis-based size tuning. In some embodiments, electrophoresis is used in combination with other enrichment methods such as silica matrix methods discussed herein. Commercial devices for electrophoretic enrichment based on size include the Pippin Prep by Sage Sciences, which comprises use of agarose gel electrophoresis. These systems can size select for nucleic acids having a minimum size of 50 bp, bases, or nt to a maximum size of 8000 bp, bases, or nt to 50,000 bp, bases, or nt. Another exemplary commercial product is based on capillary electrophoresis high-resolution size selection of nucleic acids (e.g., the Caliper Lab Chip XT).

9. Simultaneous Anion Exchange and Size Exclusion on Magnetic Beads

In some embodiments, small nucleic acids are enriched, isolated, or obtained from a sample using a method comprising preferential capture of small nucleic acids on magnetic beads comprising an amine (e.g., a weak amine) anion exchange functional group and comprising surface irregularities that result in micron and sub-micron sized pores (see, e.g., Example 4).

For example, in some embodiments, the technology utilizes a combination of size exclusion (e.g., as a result of surface and/or interior irregularities (e.g., pores and/or cavities)) and anion exchange (e.g., as a result of functionalized surface and/or interior) to selectively bind, release, and purify target nucleic acids (e.g., nucleic acids of a selected size range); although the present invention is not limited to any particular mechanism of action and an understanding of the mechanism of action is not necessary to practice the present invention. In some embodiments, microparticles are magnetic, contain functional groups that allow for anion exchange of nucleic acids, and comprise irregular surface features (e.g., pores) that allow for size-selective adherence and/or release of nucleic acids. In some embodiments, magnetic particles allow, for example, manipulation of microparticles (e.g., with or without adhered nucleic acid).

In some embodiments, a strong cation exchange functional group, such as a quaternary amine, for example, is employed as an anion exchange functional group. Additional strong anion exchange functional groups are known to those skilled in the art.

In other embodiments, a weak anion exchange functional group is a suitable anion exchange functional group, such as polyethyleneimine, a charged aromatic amine, diethylaminomethyl, or diethylaminoethyl. Such functional groups have pKa values of 9.0 or greater.

In some embodiments, the manufacturing process for microparticles creates irregularities (e.g., micron or sub-micron sized pores or cavities) on the particle surface and within the particles and/or clusters of particles. The structural irregularities (e.g., pores) on the microparticles adhere target nucleic acid products (e.g., of a desired size or size range, e.g., small nucleic acids), due to size exclusion properties, while not adhering non-target nucleic acids (e.g., nucleic acids of non-target size (e.g., larger genomic nucleic acids)). In some embodiments, surface and/or internal irregularities (e.g., pores) are functionalized with a weak anion exchange functional group the bind nucleic acids.

In some embodiments, both target and non-target nucleic acids adhere to the porous microparticles, but conditions are provided and/or adjusted to control the binding and release of the small nucleic acids to provide an enriched sample.

In certain embodiments, compositions and methods provided herein allow a user to decrease large amounts of background nucleic acid from a sample (e.g., large nucleic acids such as genomic nucleic acids).

In some embodiments, the present technology provides compositions comprising a microparticle (e.g., a bead, e.g., a magnetic bead) having a surface comprising cavities and/or other surface irregularities and/or an aggregate comprising two or more of said microparticles, which aggregate comprises an opening, wherein said surface, cavities, opening, and/or other surface irregularities/pores are: a) functionalized with a weak anion exchange functional group; and b) dimensioned for size exclusion of smaller nucleic acid molecules from larger nucleic acid molecules. In some embodiments, larger nucleic acid molecules comprise or are derived from human genomic nucleic acid. In some embodiments, compositions further comprise smaller nucleic acid molecules bound to the pores. In some embodiments, the microparticle is an iron particle. In some embodiments, the weak anion exchange functional group is an amine. In some embodiments, the amino is a primary, secondary, or tertiary alkyl amine. In some embodiments, the amine has a pKa of greater than 9. In some embodiments, the composition comprises a plurality of said microparticles.

10. Combinations of Technologies

In some embodiments, the technology comprises use, e.g., in simultaneous and/or sequential combination, of one or more of preferential elution of small nucleic acids from silica, preferential retention of large nucleic acids on silica, enrichment by MeDIP with antibody-coated particles that can be captured with a magnetic field (e.g., antibody-coated paramagnetic particles or antibody-coated magnetic particles), enrichment by size exclusion, enrichment by SCODA, enrichment by SPRI bead-based sizing, enrichment by electrophoresis-based sizing to provide a sample of small nucleic acids (e.g., DNA (e.g., cffDNA) and/or RNA) for analysis, and/or preferential capture of small nucleic acids on magnetic beads comprising an amine (e.g., a weak amine) anion exchange functional group and comprising surface irregularities that result in micron and sub-micron sized pores. In some embodiments, a silica-based enrichment method is coupled with one or more other enrichment methods to provide a sample for analysis. In some embodiments, two or more technologies are applied to a sample sequentially and in some embodiments two or more technologies are applied simultaneously. For example, in some embodiments a method for the preferential elution of small nucleic acids from silica is used at the same time with a method for the preferential retention of large nucleic acids by silica. In some embodiments, MeDIP is performed directly on a solid support (e.g., a bead, column (e.g., an affinity column), microplate, etc. comprising an agent (e.g., an antibody) specific for methylated DNA). In some embodiments, two or more technologies are applied simultaneously and additional technologies are applied sequentially.

11. Collection of Samples

The technology is not limited in the sample that is taken and enriched for small nucleic acids (e.g., DNA). For example, in some embodiments, the sample is a biological sample (e.g., taken from a subject) such as, e.g., a urine sample, a cerebrospinal fluid (CSF) sample, or a peritoneal fluid sample.

In some embodiments, a blood sample is taken. Collection of blood is performed in accordance with the standard protocol hospitals or clinics generally follow. For example, in some embodiments, an appropriate amount of peripheral blood, e.g., typically between 5 ml to 50 ml, is collected and may be stored according to standard procedure prior to further preparation. The analysis of nucleic acids found in blood may be performed using, e.g., the whole blood, serum, or plasma. The methods for preparing serum or plasma from blood are well known among those of skill in the art. For example, blood can be placed in a tube containing EDTA or a specialized commercial product such as Vacutainer SST (Becton Dickinson, Franklin Lakes, N.J.) to prevent blood clotting and plasma can then be obtained from whole blood through centrifugation. In some embodiments, serum is obtained with or without centrifugation following blood clotting. In embodiments comprising use of centrifugation, centrifugation is typically performed at an appropriate speed, e.g., 1500 to 3000×g. Plasma or serum may be subjected to additional centrifugation steps before being transferred to a fresh tube for extraction of nucleic acids. In addition to the acellular portion of the whole blood, nucleic acids may also be recovered from the cellular fraction, enriched in the buffy coat portion, which can be obtained following centrifugation of a whole blood sample from the woman and removal of the plasma.

There are numerous known methods for extracting DNA from a biological sample including blood. The general methods of DNA preparation (e.g., described by Sambrook and Russell, Molecular Cloning: A Laboratory Manual 3rd ed., 2001) can be followed; various commercially available reagents or kits, such as QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain nucleic acids from a blood sample. Combinations of more than one of these methods may also be used.

For example, in embodiments related to testing fetal nucleic acids, a blood sample is obtained from a pregnant woman at a gestational age suitable for testing using a non-invasive diagnostic method. The suitable gestational age may vary depending on the disorder tested.

12. Testing

The technology is applicable to testing small nucleic acids in a biological sample, e.g., blood, e.g., for oncology, infectious disease, fetal monitoring and testing, etc.

In some embodiments, the technology is related to genetic testing of a subject by detecting the presence or absence of a genetic marker associated with a genetic condition in the subject. In some embodiments, the technology is related to testing for the presence of an infectious entity (e.g., a bacterium, virus, eukaryotic pathogen, etc.) in a subject by detecting the presence or absence of nucleic acids associated with the infectious entity in the subject.

In some embodiments, the technology comprises non-invasive genetic testing of a fetus by detecting the presence or absence of a genetic marker associated with a genetic condition in a fetus. For example, the technology contemplates the detection of the presence or absence of a genetic marker in a fetus by detecting the presence or absence of the genetic marker in a biological sample obtained from a maternal host of a fetus. The presence or absence of the genetic marker indicates the presence or absence of the genetic condition. Moreover, the technology provides in some embodiments for detecting the presence of fetal nucleic acids in a sample from a maternal host of fetus, then testing the detected fetal nucleic acids for the presence or absence of a genetic marker associated with a disease or condition.

By "genetic marker" is meant any genetic marker known to be associated with a disease or condition, e.g., a SNP, a CNV, a gene, an allele, an enhancer, a locus, a sequence, etc. In one embodiment, the genetic marker is located within a chromosomal location conserved in cell free fetal DNA in the biological sample of the maternal host. In some embodiments, a condition is detected in a fetus by detecting the presence or absence of a marker located in just one chromosomal location. In other embodiments, a condition is detected in a fetus by detecting the presence or absence of more than one genetic marker, for example two, three, four, five, or more than five markers in one or more chromosomal locations and/or genes. In some embodiments, the genetic marker can be a mutation in the one or more chromosomal locations or genes. The mutation can be an insertion, deletion, frame shift, substitution, or any other mutations known in the art. The presence or absence of the genetic marker can be determined by any method known in the art, for example, nucleic acid sequencing, hybridization, endonuclease digestion, and/or PCR. In some embodiments, the genetic marker is detected in an RNA (e.g., a mutation is present in an RNA) and/or the amount of RNA is quantified and is indicative of a disease or condition (e.g., the amount of RNA is indicative of overexpression or underexpression of a gene or genetic marker).

In some embodiments, the presence or absence of the one or more genetic markers can be detected in enriched fetal nucleic acids derived from a whole blood sample from the maternal host of the fetus. By way of example, a whole blood sample may be taken from the maternal host of the fetus and enriched as described herein to obtain a sample of enriched fetal nucleic acids. The enriched fetal nucleic acid is then tested by any method known in the art, for example, nucleic acid sequencing or PCR, e.g., to detect the presence or absence of a genetic marker within one or more chromosomal locations and/or the amount of gene expression (e.g., RNA amounts). The results of the fetal testing done by this method may be further compared against the same testing of un-enriched whole blood derived from the mother, or fractionated nucleic acid of larger size containing maternal nucleic acids or a nucleic acid sample obtained from the maternal host prior to pregnancy to confirm the presence or absence of the genetic marker is being detected in the fetal nucleic acid and not the maternal nucleic acid. The genetic condition to be detected can be any condition.

Is some embodiments, the technology finds use in determining the sex of a fetus. In particular embodiments, the technology finds use in detecting the presence or absence of a Y chromosome in the maternal blood. For example, some embodiments provide for the detection of the gender-determining region (SRY) of the Y chromosome and/or other Y-chromosome associated loci (e.g., sequences) such as DYS, DYZ, and/or DAZ. Such tests have greater than 99% specificity and sensitivity after the 6th week of gestation and reach over 99.9% specificity and sensitivity after the 8th week of gestation. In some embodiments, determination of a female gender is correlated with the absence of a condition such as an X-linked genetic abnormality, e.g., Duchene's muscular dystrophy and hemophilia.

In some embodiments, the technology finds use in the detection of monogenic diseases having dominant paternal inheritance patterns. In such diseases, the maternal genome does not have the disease-related allele and thus its detection indicates the presence of the disease in the fetus. Examples of such conditions are Huntington's disease, achondroplasia, myotonic dystrophy, and Apert syndrome.

In some embodiments, targeted sequencing of nucleic acid enriched for nucleic acid of fetal origin provides for the noninvasive surveying of a fetal genome for mutations, alleles, etc. of interest. In some embodiments, the technology provides for the sequencing of a fetal genome.

In some embodiments, the technology finds use in determining fetal-maternal ABO (e.g., blood type) and/or Rh factor compatibility. For instance, some embodiments provide for the testing of the Rh blood group D-antigen gene (RHD), e.g., by targeting exons 4, 5, 7 and 10 of RHD, the RHD pseudogene, and a sequence for sex determination (e.g., the SRY region of the Y chromosome).

The methods of the present technology are also useful in detecting the presence or absence of aneuploidies, including monosomies or trisomies. For example, the methods of the current technology are useful in karyotype analysis, e.g., for detecting trisomy 13, 14, 15, 16, 18, 21, 22, X, and/or Y. In a specific embodiment, trisomy 21 is detected by measuring the DCR gene located at chromosome 21 q22.2-21q22.3, the CBS gene located at chromosome 21q22.2-21q22.3, the KNO gene at 21q22.3-21q22.3, and/or the SOD1 gene at chromosome 21 q22.1-21q22.1, or any combination thereof.

Fetal nucleic acids are assayed, e.g., in some embodiments by probe hybridization (FISH, etc.), PCR, sequencing (e.g., next-generation sequencing), digital counting (e.g., by next-generation sequencing; see, e.g., Chiu et al (2010) "Maternal plasma DNA analysis with massively parallel sequencing by ligation for noninvasive prenatal diagnosis of trisomy 21" *Clin Chem* 56: 459-63), nuclease digestion, probe extension, microscopy, digital PCR, real-time PCR, quantitative PCR, staining (e.g., karyotyping and banding), etc. In some embodiments, epigenetic states are assayed such as methylation and histone composition.

In some embodiments, testing comprises detecting the small fractional excess of nucleic acids (e.g., as exhibited in instances of aneuploidy (e.g., trisomy)) compared to a normal euploid fetus. In these tests, trisomy detection distinguishes 3 copies from 2 copies of a chromosome or a chromosomal fragment in a mixture where approximately 90% of the sample is euploid (e.g., disomic). In some embodiments, the fractional increase of nucleic acids in a fetal trisomy (e.g., involving chromosome 13, 18, 21, X, Y, or another chromosome) compared to a normal fetus is 1.05 or less (that is, 21 total copies for a trisomy compared to 20 copies for euploidy). In some embodiments, the ratios is 1.04 or less, 1.03 or less, or 1.02 or less.

In some embodiments, ratios of particular alleles of a placental specific nucleic acid (RNA (e.g., mRNA) or DNA) are used to detect an aneuploidy; in some embodiments, ratios of particular fetal specific methylation markers are used to detect an aneuploidy.

In some embodiments, aneuploidy is detected by molecular counting. In some embodiments, aneuploidy is detected by single molecule analysis, e.g., to count the fractional excess or shortage of nucleic acids present in the aneuploidy chromosomes relative to the remaining chromosomes present in a euploid (e.g., normal) number.

In some embodiments, allelic ratios are measured (e.g., the number of one allele relative to another allele) and a 2:1 ratio indicates an aneuploidy. In some embodiments, the copy number of one chromosome is compared to the copy number(s) of one or more other chromosomes in the genome. Using such a method, the ratio of a trisomic aneuploid chromosome to a disomic euploid chromosome is expected to be 3:2 (a value of 1.5) and the ratio of a monosomic aneuploid chromosome to a disomic euploid chromosome is expected to be 1:2 (a value of 0.5).

In the presence of background diploid maternal DNA (e.g., as in most maternal DNA plasma samples), the ratio for trisomy is smaller than 1.5 but is greater than 1 and the ratio for monosomy is greater than 0.5 but less than 1. In samples with a high amount of background maternal nucleic acid (e.g., in an unenriched sample comprising approximately 10% or less than 10% (e.g., 5 or 6%) fetal nucleic acid, these values approach 1.0 (e.g., slightly more than 1.0 for trisomy and slightly less than 1.0 for monosomy). As the amount of fetal nucleic acid in a sample increases in proportion to the background maternal nucleic acid (e.g., in an enriched sample as provided by the present technology), the ratio of a trisomic aneuploid chromosome to a disomic euploid chromosome approaches 1.5 and the ratio of a monosomic aneuploid chromosome to a disomic euploid chromosome approaches 0.5. Thus, the enrichment technology described herein provides improved methods for detecting aneuploidies because the ratios indicative of aneuploidy (e.g., values closer to 1.5 or 0.5) are more different than the euploid 1.0 ratio (and thus easier to detect) than are the ratios that are indicative of aneuploidy in a non-enriched sample (e.g., values closer to, and thus less distinguishable from, 1.0 for both trisomies and monosomies).

The overrepresentation or underrepresentation of the aneuploid chromosome is detectable by counting a number of chromosomes (or, e.g., chromosomal markers, alleles, genes, etc.) that is greater than the statistically predictable threshold of noise in the sample.

In maternal blood, most cell-free DNA is derived from the mother, who typically has a normal genotype (e.g., is euploid). For a trisomic fetus, the fraction of fetal DNA in maternal plasma is f, the ratio of the number of copies of the trisomic chromosome to a euploid chromosome is 1+f/2, and the difference between the number of copies of the trisomic chromosome and the number of copies r of a reference chromosome is rf/2.

This fractional increase in the trisomic chromosome is detectable provided that the number of molecules counted provides resolution of the signal relative to the noise, which scales as the square root of the counts according to the Poisson distribution (e.g., assuming the normal approximation of the Poisson distribution and that the variance of the Poisson distribution with mean N is N) and the following equations:

$$r = \frac{4\left(a\sqrt{2} + b\sqrt{2 + \frac{f}{2}}\right)^2}{f^2} \quad (1)$$

where f is the fraction of fetal nucleic acid (DNA) in maternal plasma, r is the number of copies of a reference chromosome, and a and b are provided as follows:

$$a = \frac{c - 0}{\sqrt{2r}} \quad (2a)$$

$$-b = \frac{c - (a - r)}{\sqrt{a + r}} \quad (2b)$$

where c is the cutoff value for detecting a difference between the number of reference chromosomes r and the number of abnormal chromosomes a (e.g., a−r>0). The values a and b are related to the false positive error rate and the false negative error rate, respectively. The values a and r are related by the equation:

$$a = r\left(1 + \frac{f}{2}\right) \quad (3)$$

According to these equations 1-3, the number of reference chromosomes that is required to be counted (r) depends on the fetal DNA fraction (f) and the sensitivity and specificity (related to a and b). Consequently, the lower the fraction of fetal nucleic acid in maternal blood, the more counts are needed to discriminate aneuploidy from euploidy. And, consequently, the higher the fraction of fetal nucleic acid in maternal blood (e.g., at the same given sensitivity and specificity), fewer counts (e.g., fewer digital PCR reactions, fewer sequencing reactions and less sequence information, etc.) are needed to discriminate aneuploidy from euploidy. See, e.g., Fan, Hei-Mun Christina, Stephen Ronald Quake, Russ Altman, and Markus Covert, "Molecular Counting: From Noninvasive Prenatal Diagnostics to Whole-Genome Haplotyping" Thesis (Ph.D.)—Stanford University, 2011, incorporated herein by reference in its entirety.

In some embodiments, chromosomal counting is performed by digital PCR. In some embodiments, chromosomal counting is performed by sequencing. In some embodiments, chromosomal counting is performed by fluorescent in situ hybridization or other probe-based method. In some embodiments, chromosomal counting is performed by quantitative-fluorescent PCR. In some embodiments, the number of amyloid genes (representing the copy number of chromosome 21) is compared to the number of GAPDH genes (representing the copy number of a reference chromosome (chromosome 12)). Other chromosomal markers and haplotypes for any human chromosome are known in the art.

In some embodiments, the technology comprises obtaining, enriching, and/or isolating small nucleic acids (e.g., small DNA (e.g., cffDNA) and/or RNA), and testing the small nucleic acids in combination with performing one or more other tests such as amniocentesis, chorionic villus sampling, placental biopsy, cordocentesis, cytogenetic diagnosis, nuchal translucency screening, assessment of biochemical parameters (e.g., human chorionic gonadotropin, pregnancy-associated plasma protein, alpha fetoprotein, free estriol, inhibin A, fetal biometry, etc.).

In some embodiments, the information obtained from assessing fetal nucleic acids present in the maternal blood is used to inform an antenatal intervention and/or medical care delivery to the fetus. In some embodiments, the information obtained from assessing fetal nucleic acids present in the maternal blood suggests a post-delivery intervention and/or medical care delivery to the child.

In some embodiments, the technology is related to testing a subject for a cancer. Genetic abnormalities (e.g., somatic DNA mutations such as single-base substitutions, insertions, deletions, and translocations (e.g., gene fusions, gene amplifications, and/or losses of heterozygosity)) associated with cancers provide a specific biomarker for cancers that are detected and monitored to diagnose and treat cancers. Tumor cells associated with cancers release nucleic acids (e.g., small nucleic acids) comprising somatic mutations into the bloodstream (see, e.g., Bettegomda, et al (2014) "Detection of circulating tumor DNA in early- and late-stage human malignancies" Sci Transl Med. 6(224): 224ra24, incorporated herein by reference in its entirety). In some cases, dying tumor cells release small pieces of DNA into the bloodstream, which are sometimes referred to as "cell-free circulating tumor DNA (ctDNA)". Thus, as used herein, "ctDNA" refers to small fragments of nucleic acid that are not associated with cells or cell fragments and that provide a biomarker associated with a cancer.

Thus, in some embodiments, the technology relates to the non-invasive detection of a cancer biomarker—e.g., the technology provides a method to detect biological molecules (e.g., small nucleic acids, such as small circulating cell-free DNA) in a sample (e.g., in the blood) that indicate the presence of a cancer or that indicate the likelihood that a cancer will develop. Accordingly, embodiments of the technology are used as a cancer diagnostic (e.g., to assess a risk of cancer; to detect the presence of cancer (e.g., to detect a neoplasm, to detect a cancerous cell, to detect a tumor); to detect a genetic state associated with a cancer; to determine a predisposition to develop a cancer in the future).

In some embodiments, the technology relates to detecting a small nucleic acid biomarker for cancer from a patient sample and indicating a stage (e.g., stage I, stage II, stage III, or stage IV) of a cancer. In some embodiments, the amount (e.g., mass, concentration, weight (e.g., in absolute or relative terms)) of a small nucleic acid cancer biomarker in the blood correlates with the amount of metastasis of a cancer or the stage of a cancer (e.g., the concentration in blood of a small circulating cell-free DNA comprising a cancer biomarker increased as the amount of metastasis and/or cancer stage increased). In some embodiments, a circulating cell-free DNA comprising a cancer biomarker (e.g., ctDNA) is found at a relatively high concentration in the circulation of a patient with a metastatic cancer and a circulating cell-free DNA comprising a cancer biomarker (e.g., ctDNA) is detected at a lower but detectable concentration in a patient with a localized cancer.

In some embodiments, quantifying and monitoring the level of small circulating cell-free DNA comprising a cancer biomarker indicates the progression and/or stage of a cancer. In some embodiments, the technology provides for monitoring tumor progression and testing the response of a tumor to drug treatments. In some embodiments, the technology finds use to monitor patients being treated with targeted agents and/or to detect recurrence and/or to provide information relating to the genetic basis of resistance to one or more drugs used for cancer treatment.

In some embodiments, the technology provides for the detection, diagnosis, monitoring, and/or treatment of pancreatic, ovarian, colorectal, bladder, gastroesophageal, breast, melanoma, hepatocellular, and/or head and neck cancer. In some embodiments, the technology provides for the detection, diagnosis, monitoring, and/or treatment of brain, renal, prostate, and/or thyroid cancer. In some embodiments, small circulating cell-free DNA comprising a cancer biomarker (e.g., ctDNA) is detectable in a patient sample that does not comprise detectable circulating tumor cells. In some embodiments, small circulating cell-free DNA comprising a cancer biomarker (e.g., ctDNA) is detectable in a patient sample that comprises detectable circulating tumor cells. In some embodiments, small circulating cell-free DNA comprising a cancer biomarker (e.g., ctDNA) is detectable in a patient sample that does not comprise a detectable protein biomarker of a cancer.

In some embodiments, small circulating cell-free DNA is isolated according to the technology provided herein and a cancer biomarker is detected using, e.g., amplification (e.g., PCR), sequencing (e.g., targeted sequencing, exomic sequencing, and/or whole-genome sequencing), single-base extension, hybridization, etc., to identify mutations associated with cancer (e.g., to detect or identify a biomarker).

Cancer biomarkers associated with particular cancers are known in the art (see, e.g., Schwarzenbach, et al (2011) "Cell-free nucleic acids as biomarkers in cancer patients", Nature Reviews Cancer 11, 426-437, incorporated herein by reference in its entirety). For example, KRAS, BRAF, NRAS, and PIK3CA are known somatic cancer biomarkers. Other exemplary somatic cancer and/or tumor biomarkers include, but are not limited to, ALK, B-raf, EGFR, K-ras, N-ras, AKT1, PIK3CA, Her2, FGFR1, FGFR2, FGFR3, MEK, c-Met, PTEN, ROS-1, DDR, RET, and c-kit.

In some embodiments, the technology is related to detecting the presence of or methylation state of a Septin 9 biomarker associated with colorectal cancer—in some embodiments, detecting methylation of the Septin 9 promoter region (e.g., in small circulating cell-free DNA comprising the Septin 9 promoter region) provides for the detection of colorectal cancer in a patient. In some embodiments, the technology provides for the isolation of Septin 9 small circulating cell-free DNA.

In some embodiments, the small nucleic acid biomarker associated with cancer provides information related to cancer prognosis (e.g., the small nucleic acid biomarker provides information related to the stage of cancer), cancer diagnosis, choice of cancer therapy (e.g., surgery, radiotherapy, chemotherapy, other pharmaceutical therapies, etc.), and/or predicting a response of a subject to a cancer therapy.

13. Subjects

Furthermore, in some embodiments, the technology finds use in processing a sample obtained from a subject, e.g., blood obtained from a subject (e.g., a pregnant mother, an oncology patient, a subject having or suspected of having an infectious disease) for analysis of the state (e.g., genetic state, cancer state, infection state) of the subject or of a gestating fetus.

In some embodiments, a subject is selected and/or tested based on risk factors associated with the subject's age. In particular, the incidence of some genetic disorders (e.g. in a gestating fetus or in the subject (e.g., a cancer or neoplasm in the subject)) increases with the age of the subject.

In some embodiments, the subject has an age that is greater than 30, 31, 32, 33, 34, 35, 36, 37, 38, 39, 40, 41, 42, 43, 44, 45, 46, 47, 48, 49, or 50 years. In some embodiments, a subject is selected based on a result (e.g., an abnormal result) of a previous invasive or non-invasive test, such as an ultrasound, amniocentesis, chorionic villus sampling and testing, etc. In some embodiments, one or both parents has or have a known genetic abnormality (e.g., a translocation, inversion, point mutation, insertion, deletion, etc.), thus providing a criterion for selecting a subject from whom to collect and test cffDNA. In some embodiments, an existing child has a known genetic abnormality (e.g., a translocation, inversion, point mutation, insertion, deletion, etc.), thus providing a criterion for selecting a subject from whom to collect and test cffDNA of the sibling fetus. In some embodiments, a combination of two or more of these risk factors indicates the presence of a higher risk such that blood from the subject pregnant mother should be obtained and the cffDNA tested.

EXAMPLES

Example 1—Small DNA Fragment Enrichment by Reverse SPRI

During the development of embodiments of the technology provided herein, experiments were conducted to test the enrichment of small nucleic acids in a sample using SPRI. In particular, SPRI beads were used to bind and remove large nucleic acids from a sample, thus enriching the remaining liquid sample for non-bound small nucleic acids (e.g., "reverse SPRI"). Recovery of nucleic acids was evaluated using a test sample comprising a ladder of nucleic acids (E-gel 25 bp DNA ladder, Life Technologies catalogue number 10488095) having sizes of 25 bp, bases, or nt; 50 bp, bases, or nt; 75 bp, bases, or nt; 100 bp, bases, or nt; 115 bp, bases, or nt; 125 bp, bases, or nt; 150 bp, bases, or nt; 175 bp, bases, or nt; 200 bp, bases, or nt; 225 bp, bases, or nt; 250 bp, bases, or nt; 275 bp, bases, or nt; 300 bp, bases, or nt; 325 bp, bases, or nt; 350 bp, bases, or nt; 375 bp, bases, or nt; 400 bp, bases, or nt; 425 bp, bases, or nt; 450 bp, bases, or nt; 500 bp, bases, or nt; and 2652 bp, bases, or nt.

Recovery of fragments from the sample was tested using an in-house SPRI bead protocol (Abbott Molecular ("AM") SPRI) and two commercial kits. The commercial kits tested were the Qiagen QIAamp Circulating Nucleic Acid (CNA) kit and Beckman Coulter Agencourt AMPure XP. The AM SPRI protocol for enrichment of small nucleic acids (e.g., 50 bp to 500 bp) comprised the following steps. First, 250 ng of a test sample (25 bp ladder) was diluted to 1 ml using de-ionized water. To this diluted sample, 750 µl of AM-bind-A buffer (18% PEG-8000, 1 M NaCl, 10 mM Tris-HCl (pH ~8), 1 mM EDTA) containing 1 µM carboxyl-modified beads (Sera-Mag Magnetic SpeedBeads Carboxylate-Modified, Thermo Scientific) at 1 mg/ml beads was added (e.g., a 1:0.75 ratio of sample:AM-bind-A) and mixed well by pipetting up and down approximately 10 times. This mixture was incubated at room temperature for approximately 5 minutes and put on a magnetic rack for approximately 7 minutes. A volume of 1.6 ml of supernatant was carefully transferred to a new tube. To the supernatant, 4 ml of AM-bind-B buffer (14% PEG-8000, 1.2 M NaCl, 6 mM Tris-HCl (pH ~8), 0.6 mM EDTA, 39% iso-propyl alcohol) was added (1:2.5 ratio of supernatant:AM-bind-B) and mixed well by pipetting up and down approximately 10 times. This mixture was incubated at room temperature for approximately 10 minutes and put on a magnetic rack for approximately 7 minutes. With the tube remaining in the magnetic rack, the supernatant was carefully pipetted out and discarded. With the tube still remaining in the magnetic rack, the beads were washed two times using 300 µl of 75% ethanol per wash. At the end of the 2nd wash, the ethanol was removed without disturbing the beads. The beads were air-dried for approximately 5 minutes and re-suspended in 50 µl of low Tris-EDTA buffer (10 mM Tris-HCl, 1 mM EDTA (pH ~8)) off of the magnetic rack. The tube with the re-suspended beads was placed back on the magnetic rack for approximately 1 minute. Finally, the supernatant, which comprises the small DNA fragment enriched product, was transferred to a new tube without disturbing the beads (e.g., approximately 98 µl of supernatant was removed rather than the entire 100 µl). A volume of 1 µl of this supernatant was used for DNA fragment analysis, e.g., using Agilent's Bioanalyzer 2100 with High-Sensitivity DNA chips.

Small DNA fragment enrichment using the test sample as described above and commercial kits (e.g., Qiagen QIAamp Circulating Nucleic Acid (CNA) kit and Beckman Coulter Agencourt AMPure XP (Gel-free DNA size selection)) was performed following the protocols provided by the respective vendors. The final products were used for DNA fragment analysis, e.g., using an Agilent Bioanalyzer 2100 with High-Sensitivity DNA chips.

The data collected during the experiments indicated that nucleic acids having a size of 100 bp, bases, or nt or less were efficiently captured using the AM SPRI (FIG. 1). No nucleic acids of 100 bp, bases, or nt or less were captured by AMPure XP (FIG. 1). FIG. 1 shows the amount of each fragment size (first row of the table) present in the input sample in picograms (second row of the table) and the amount recovered of each fragment using the three enrichment methods (third, fourth, and fifth rows of the table). In addition, very small amounts of sample are more efficiently captured by the AM SPRI method compared to the Qiagen QIAamp Circulating Nucleic Acid kit and the AMPure XP kit.

Further, experiments were conducted to assess the enrichment of small nucleic acids by these three methods. In particular, enriched samples were analyzed by comparing the fraction of small DNA in the enriched samples to the input test sample comprising a ladder of nucleic acids. Data were collected before (FIG. 2A) and after enrichment with a commercial kit designed to isolate free-circulating DNA and RNA from human plasma or serum (Qiagen Circulating Nucleic Acid kit, FIG. 2B) and two types of SPRI beads (Beckman AMPure, FIG. 2C; AM SPRI, FIG. 2D). The amounts of each fragment of the test sample were quantified before and after enrichment using gel electrophoresis and densitometric analysis of gel images.

Figure 2A:
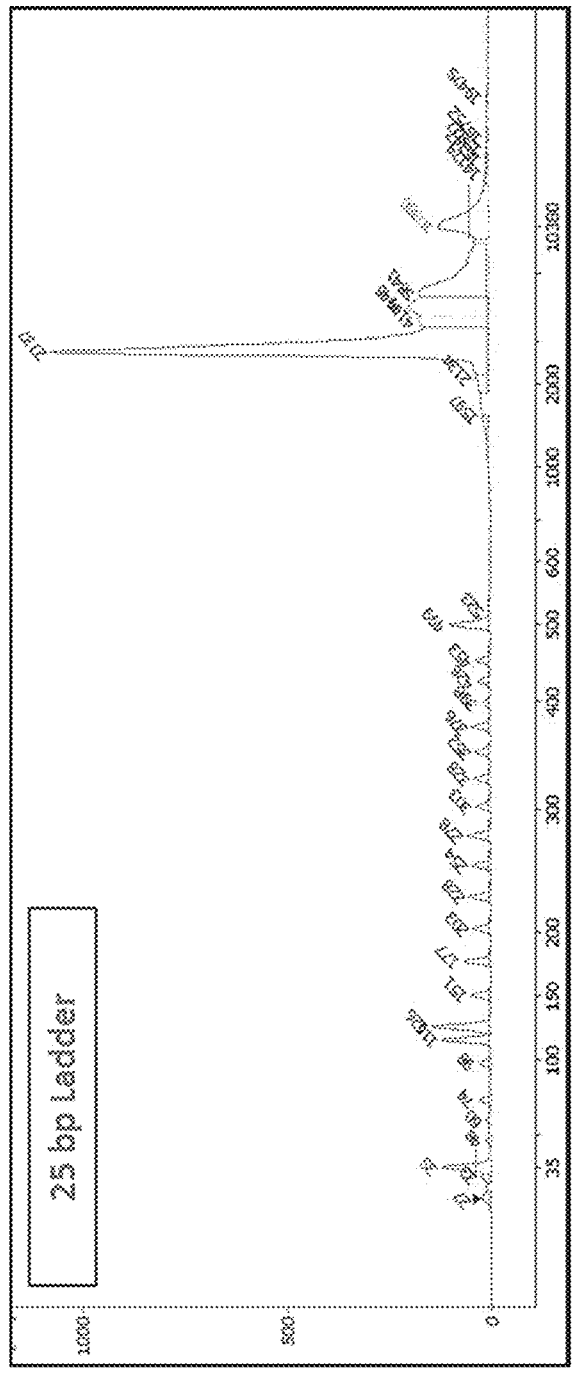
FIG. 2A-2E is a series of plots showing the uniform enrichment small nucleic acids using "reverse SPRI" methodology relative to other techniques.
Figure 2B:
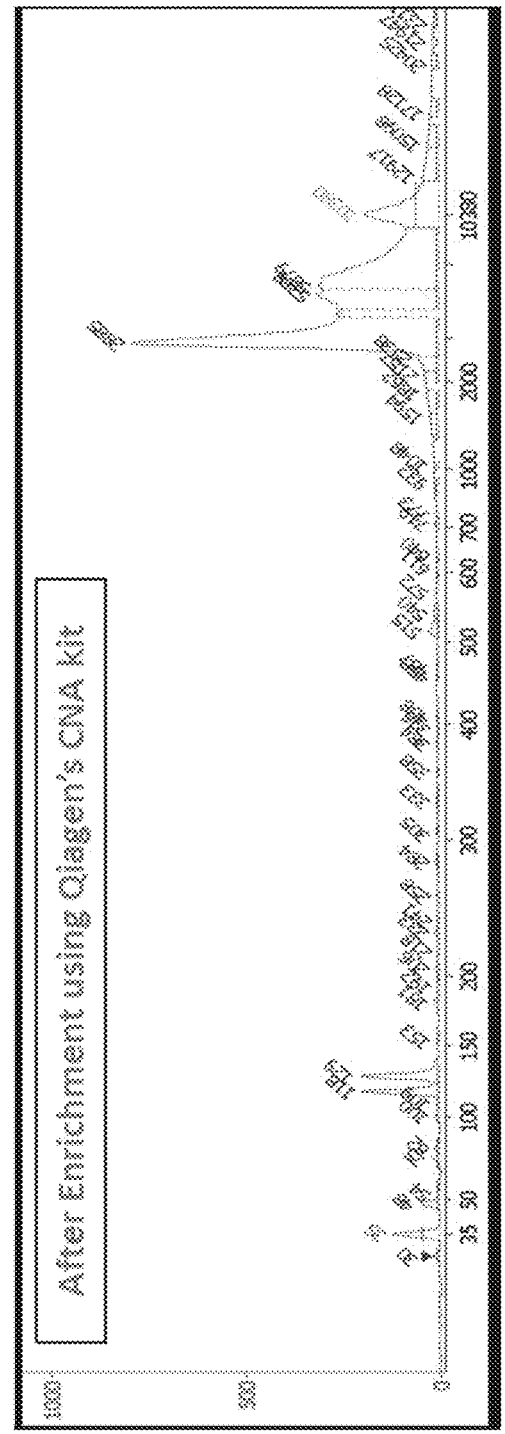
Figure 2C:
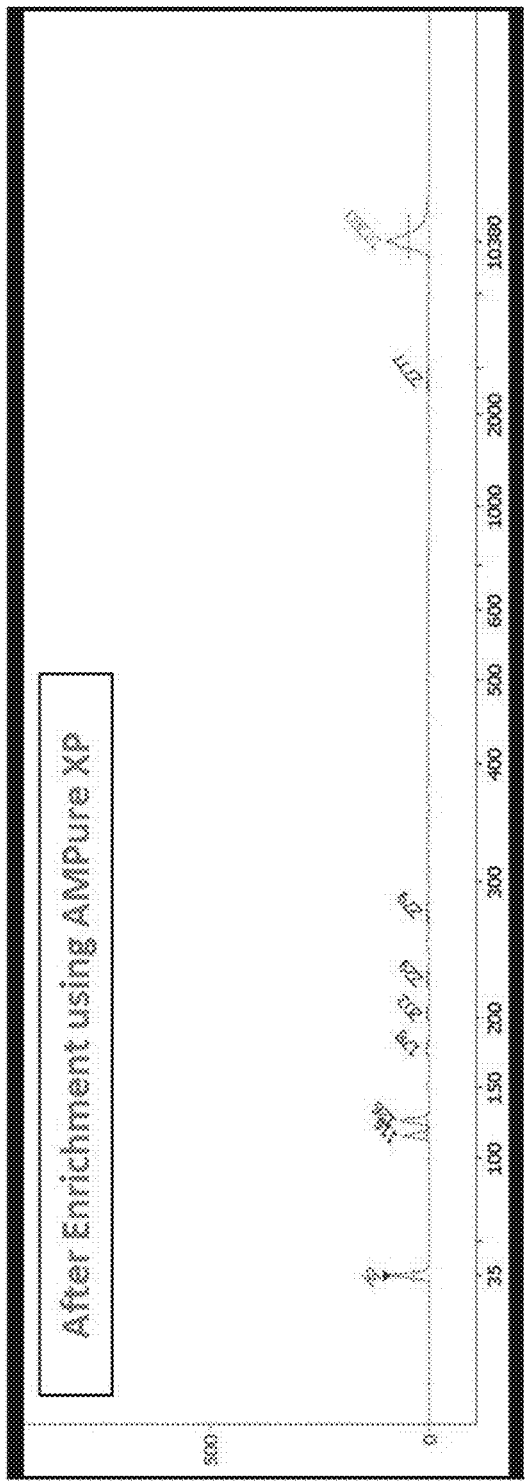
Figure 2D:
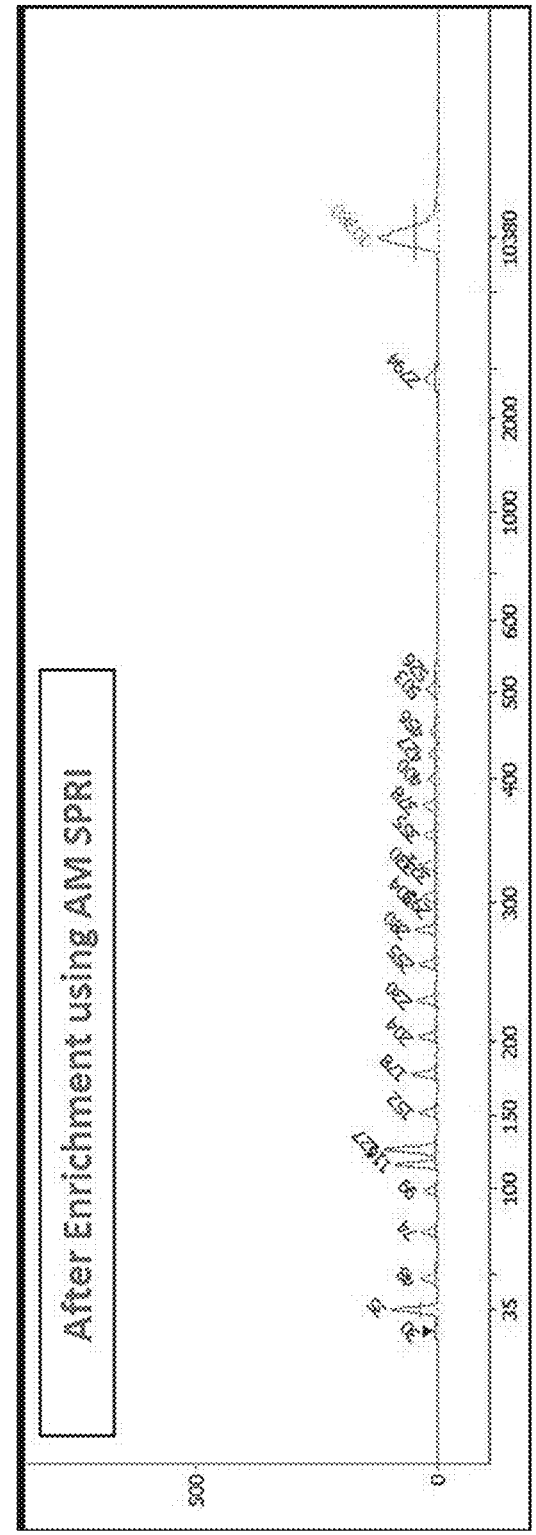
Figure 2E:
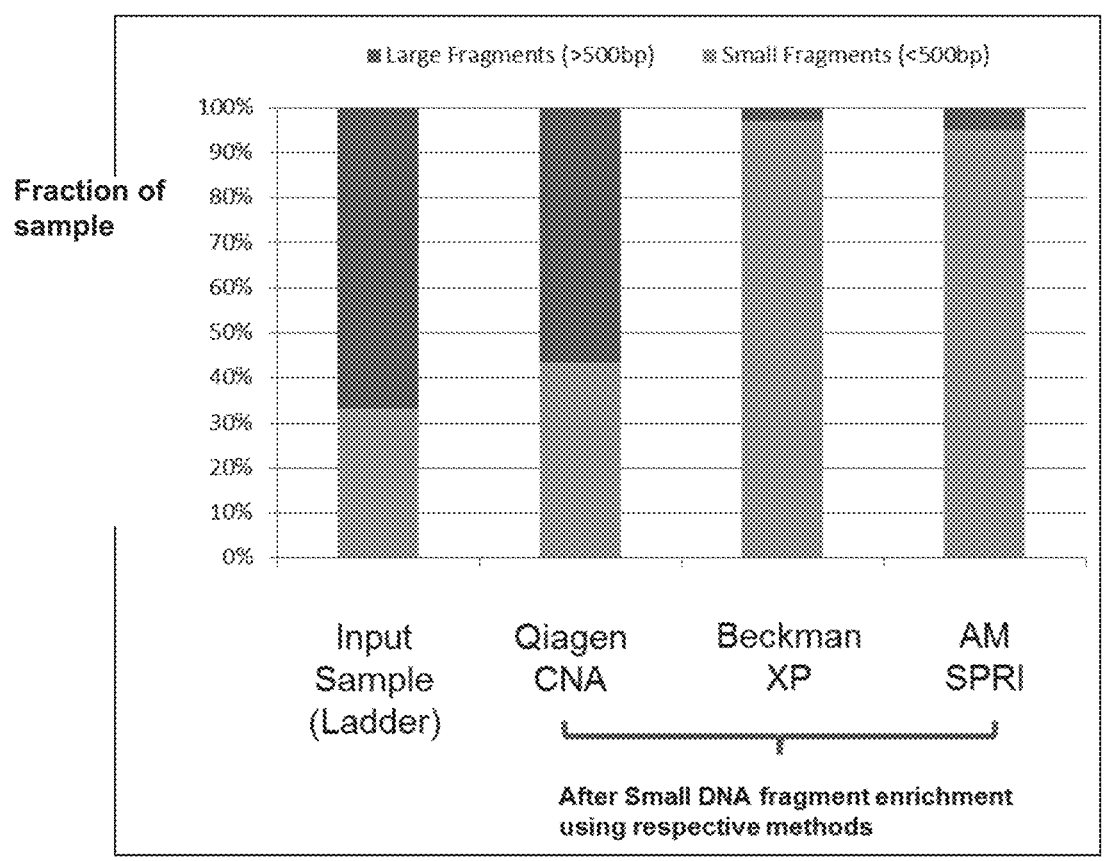

The data collected showed that both the AMPure and the AM SPRI methods provided an enrichment of small fragments (e.g., less than 500 bp, bases, or nt) of approximately 150% (FIG. 2E). Specifically, the input test sample comprised 20.2 ng of DNA in fragments less than 500 bp, bases, or nt and 32.0 ng of DNA in fragments greater than 500 bp, bases, or nt, which is a ratio of 38.7% fragments less than 500 bp, bases, or nt relative to fragments greater than 500 bp, bases, or nt. The sample enriched by AMPure comprised 3.3 ng of DNA in fragments less than 500 bp, bases, or nt and 0.1 ng of DNA in fragments greater than 500 bp, bases, or nt, which is a ratio of 97.0% fragments less than 500 bp, bases, or nt relative to fragments greater than 500 bp, bases, or nt. The sample enriched by AM SPRI comprised 11.6 ng of DNA in fragments less than 500 bp, bases, or nt and 0.6 ng of DNA in fragments greater than 500 bp, bases, or nt, which is a ratio of 95.1% fragments less than 500 bp, bases, or nt relative to fragments greater than 500 bp, bases, or nt. These data indicate a 150% enrichment by the AMPure method and a 146% enrichment by the AM SPRI method.

While the AMPure and AM SPRI methods provided similar enrichment of small fragments, the AM SPRI method yielded a distribution of small fragments that reflected the input sample composition more evenly and uniformly than the AMPure method (Compare FIG. 2A with FIG. 2C (AMPure) and FIG. 2D (AM SPRI)). Data collected showed that the AMPure method provided uneven enrichment of small fragments and did not enrich fragments less than 75 bp, bases, or nt (Compare FIG. 2A with FIG. 2C). The AM SPRI method provided a more uniform enrichment of small fragments, including fragments less than 75 bp, bases, or nt (Compare FIG. 2A with FIG. 2D).

Example 2—PEG Concentration Contributes to Size Selection

Figure 3:
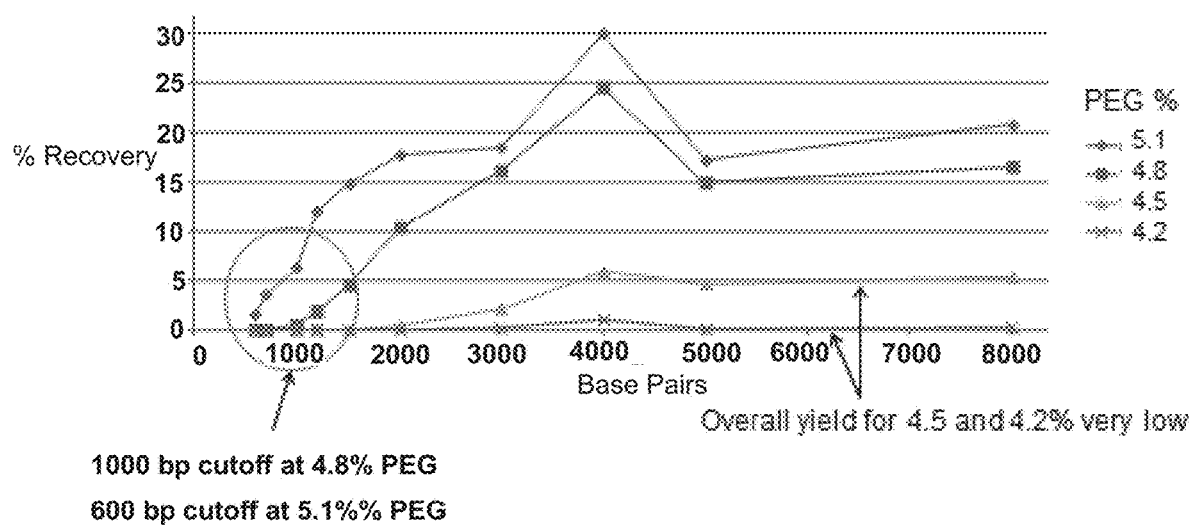
FIG. 3 is a plot showing that reducing the concentration of polyethylene glycol in buffers reduces the recovery of smaller nucleic acids.

During the development of embodiments of the technology provided herein, experiments were conducted to assess recovery of small nucleic acids as a function of PEG concentration in buffers used for SPRI bead-based depletion of large DNA. Magnamedics MagSi DNA-binding beads were used for DNA binding, the test sample comprised 500 ng DNA ladder, and PEG 8000 was used in buffers at 5.1%, 4.8%, 4.5%, and 4.2% (weight per volume). The data collected showed that reducing the PEG % reduces the recovery of smaller (e.g., lower molecular weight) DNA (FIG. 3). The overall yields for 4.5% and 4.2% PEG were very low (FIG. 3). A concentration of 5.1% PEG produced a cutoff at about 600 bp, bases, or nt, e.g., nucleic acids larger than 600 bp, bases, or nt were bound to beads and removed from the sample; nucleic acids smaller than 600 bp, bases, or nt remained in the sample, which was then enriched for small nucleic acids less than 600 bp, bases, or nt. A concentration of 4.8% PEG produced a cutoff at about 1000 bp, bases, or nt, e.g., nucleic acids larger than 1000 bp, bases, or nt were bound to beads and removed from the sample; nucleic acids smaller than 1000 bp, bases, or nt remained in the sample, which was then enriched for small nucleic acids less than 1000 bp, bases, or nt.

Example 3—Size Selection Using a Silica Column

During the development of embodiments of the technology provided herein, experiments were conducted to test the effects of elution buffer and wash buffer components on the preferential recovery of small nucleic acids from total bulk DNA. Experiments quantified the amounts of differently sized nucleic acids from a DNA ladder before and after binding to and elution from silica under varying buffer conditions.

The input sample was a DNA comprising a range of sizes (approximately 100 bp, bases, or nucleotides to approximately 8000 bp, bases, or nucleotides). The sample was flowed over the column to bind nucleic acids to the column. The column (comprising bound nucleic acids) was then washed with a wash buffer. After washing the column with the wash buffer, some DNA remains adsorbed to the column (e.g., preferential adsorption of large nucleic acids under the wash conditions) and some DNA is removed from the column and is present in the wash buffer (e.g., preferential released of small nucleic acids from the column under the wash conditions). Then, an elution buffer is flowed over the column to remove DNA from the column that remained bound during the wash. Thus, the preferential binding of DNA (e.g., large DNA) to the column during the wash step will produce an eluate enriched for large DNA and a wash buffer enriched for small DNA. Thus, an increase of recovery of large DNA in the eluate indicates that the wash buffer flow-through was enriched for small DNA.

Data indicated that size selection is provided by adjusting wash buffer components and/or concentrations. To test size selection using a silica membrane, several ratios of wash buffer to sample volume were tested to assess the stabilized binding of large DNA to the silica during the wash step, which allows smaller DNA to be recovered in the wash buffer prior to eluting the large DNA in the elution buffer. Two wash buffers were tested: 70% ethanol (see FIG. 4A) and wash buffer comprising Tween-20, ethanol, and $MgCl_2$ (e.g., "T10/15/20", which is a wash buffer comprising 10% Tween-20, 15% ethanol, and 20 mM $MgCl_2$) (see FIG. 4B). 70% ethanol was tested at ratios of 0.5:1, 0.4:1, and 0.3:1; buffer T10/15/20 was tested at ratios of 0.5:1 and 0.4 to 1.

Figure 4A:
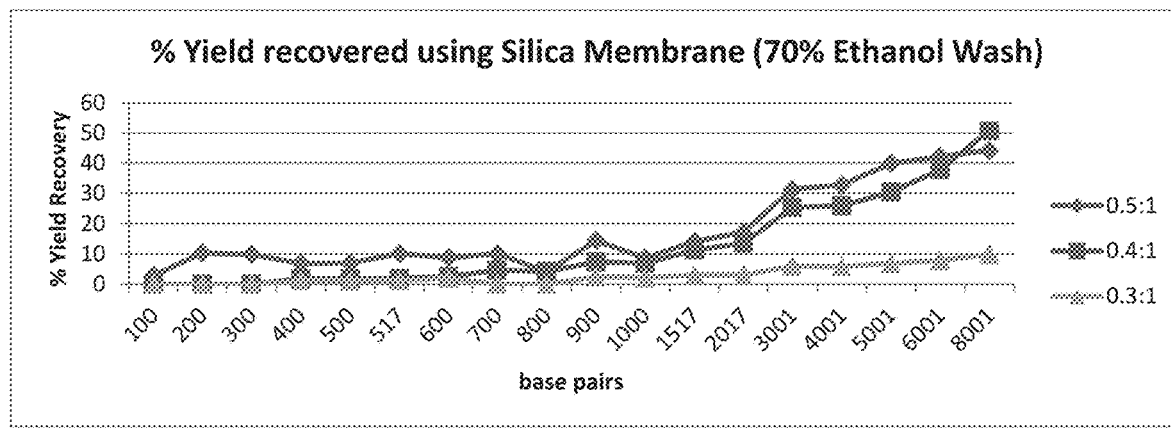
FIG. 4A-4B is a series of plots showing the size selection on silica columns as a function of the type and volume of wash buffer used.

The data show increased recovery (based on % yield) of large nucleic acids in the eluate when the column was washed with a wash buffer comprising 70% ethanol at a wash buffer to sample volume ratio of 0.5 to 1 and at a wash buffer to sample volume ratio of 0.4 to 1 (FIG. 4A). Less recovery of large nucleic acids in the eluate was detected using 70% ethanol as a wash buffer at a wash buffer to sample volume ratio of 0.3 to 1. As such, the data indicate that 70% ethanol wash buffer was enriched for small nucleic acids at a wash buffer to sample volume ratio of 0.5 to 1 and at a wash buffer to sample volume ratio of 0.4 to 1 and to a lesser extent at a wash buffer to sample volume ratio of 0.3 to 1.

Figure 4B:
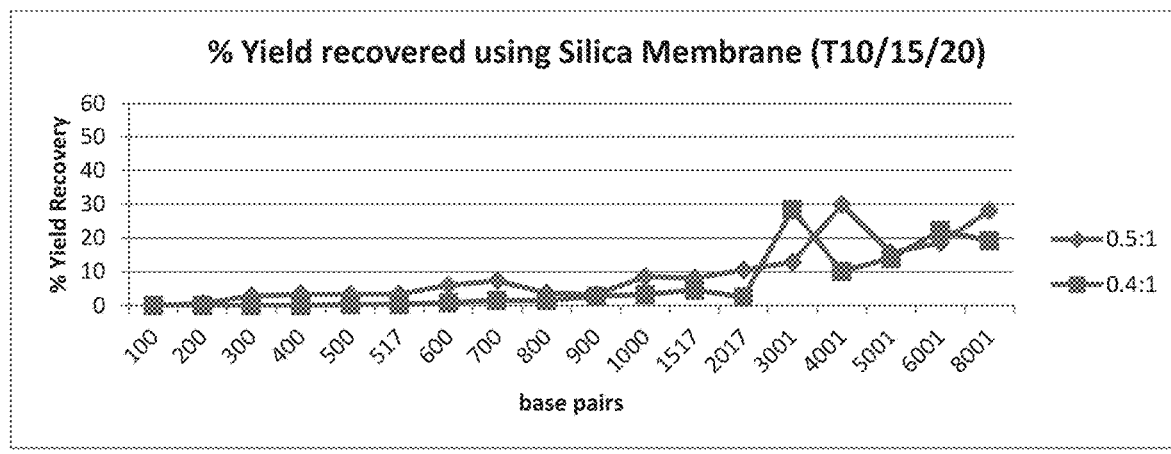

Similarly, the data show increased recovery (based on % yield) of large nucleic acids in the eluate when the column was washed with a wash buffer comprising Tween-20, ethanol, and $MgCl_2$ (T10/15/20 buffer) at a wash buffer to sample volume ratio of 0.5 to 1 and at a wash buffer to sample volume ratio of 0.4 to 1 (FIG. 4B). As such, the data indicate that T10/15/20 wash buffer was enriched for small nucleic acids at a wash buffer to sample volume ratio of 0.5 to 1 and at a wash buffer to sample volume ratio of 0.4 to 1. Thus, the wash buffer comprising Tween-20, ethanol, and $MgCl_2$ results in an enrichment of small nucleic acids (e.g., less than 1000 bp, e.g., less than 500 bp, e.g., less than 300 bp) relative to large nucleic acids.

In sum, these experiments demonstrate enrichment of small DNA (e.g., fragments less than 200 bp, bases, or nt) by SPRI methods (e.g., "reverse SPRI") and on-column DNA size selection. Conventional SPRI cleanup protocols do not adequately enrich for small nucleic acids (e.g., less than 200 bp, bases, or nt) while minimizing large DNA fragment carryover (e.g., greater than 200 bp, bases, or nt). The use of AM SPRI buffer and carboxyl-modified magnetic beads provides more uniform enrichment of fragments less than 75 to 100 bp, bases, or nt relative to conventional SPRI, while maintaining selection against large nucleic acids greater than 500 bp, bases, or nt. In addition, increased PEG (8000 MW) results in increased yield of smaller nucleic acids (4.8% PEG minimizes or eliminates recovery of nucleic acids below 1000 bp, bases, or nt; 5.1% PEG minimizes or eliminates recovery of nucleic acids below 600 bp, bases, or nt). Adjusting the wash buffer composition provides for size selection directly on the surface of silica spin-columns.

Example 4—Size Selection by Anion Exchange and Size Exclusion

During the development of embodiments of the technology, experiments were conducted to compare enrichment of samples for small DNA using beads having a rough surface (e.g., beads comprising surface irregularities that result in micron and sub-micron sized pores) and beads having a relatively smooth (e.g., smoother) surface. As used herein, a "bead having an irregular surface" or "a bead comprising surface pores" refers to a particle (e.g., a nucleic acid capture particle) having surface pores that provide size exclusion properties to the bead appropriate for the enrichment of small nucleic acids in a sample (e.g., pores that are only accessible to nucleic acids of the target size, e.g., small nucleic acids). For example, in some embodiments a "bead having an irregular surface" or "a bead comprising surface pores" refers to a particle (e.g., a nucleic acid capture bead) comprising pores having a dimension of approximately 1 to 10 microns or pores having a dimension of approximately less than a micron (e.g., pores having a dimension of approximately 1 to 1000 nanometers or smaller). Accordingly, as used herein, "a bead having a smooth surface" refers to a particle (e.g., a nucleic acid capture particle) that does not have surface irregularities and/or that does not have surface pores that provide size exclusion properties to the bead appropriate for the enrichment of small nucleic acids in a sample. For example, in some embodiments "a bead having a smooth surface" does not have pores having a dimension of approximately 1 to 10 microns, e.g., in some embodiments in which the particles have pores, the pores have a dimension of greater than approximately 1 to 10 microns. In some embodiments, the beads comprising surface irregularities that result in micron and sub-micron sized pores also comprise an amine (e.g., a weak amine) anion exchange functional group.

Figure 5:
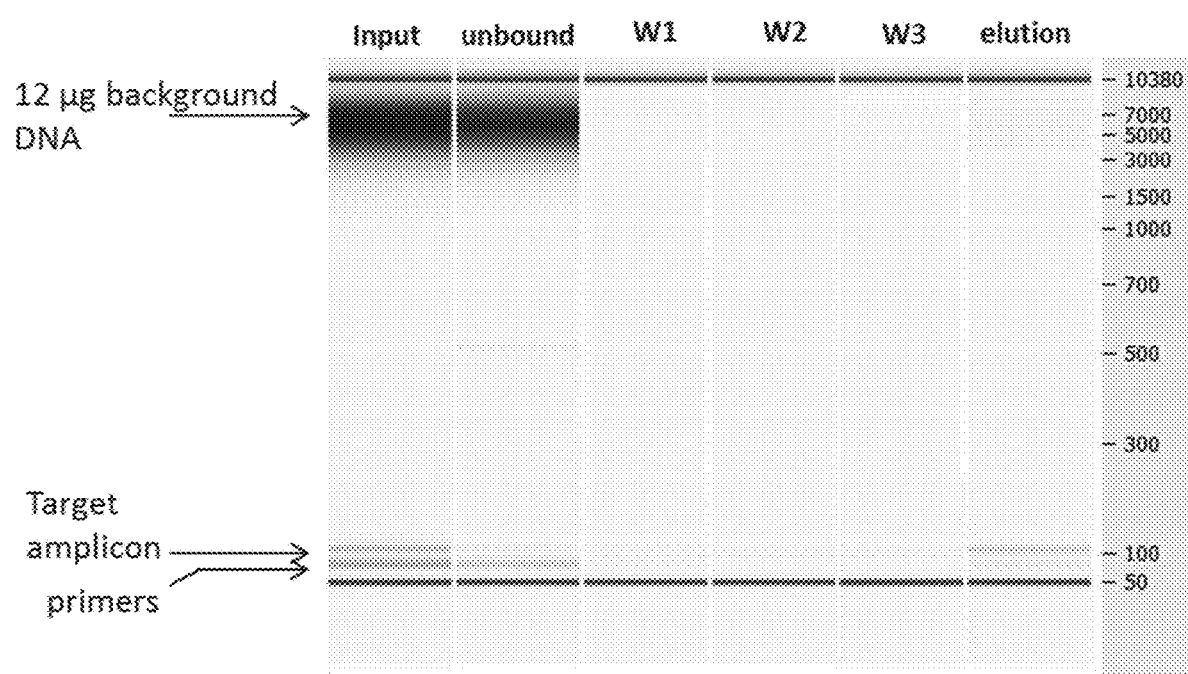
FIG. 5 shows capillary electrophoresis data for enrichment of small nucleic acids using magnetic beads.

Data were collected from capillary electrophoresis analysis experiments that measured the polynucleotide components of a post-PCR reaction (e.g., comprising small nucleic acid in the form of amplicons) that contained 12 μg of human DNA before enrichment (FIG. 5, "Input"). A four-minute incubation in the presence of amine magnetic beads allowed preferential binding of small nucleic acid (e.g., the target amplicon) while a majority of the background DNA and primers did not bind (FIG. 5, "unbound"). After three washes (FIG. 5, "W1", "W2", and "W3"), the small nucleic acids (e.g., target amplicons) were eluted from the beads while the remaining background DNA did not elute in appreciable quantities relative to its starting amount (FIG. 5, "elution"). These data indicate that the majority of non-target background nucleic acid does not bind to the amine magnetic beads while the target small nucleic acids are efficiently bound and eluted, thus provided a sample enriched for small nucleic acids.

Furthermore, data were collected indicating that adequate removal of large nucleic acids is associated with the use of magnetic beads having an irregular surface contour. In particular, nucleic acid capture by magnetic beads functionalized with an amine group and having an irregular surface contour was compared to nucleic acid capture by magnetic beads functionalized with an amine group and having a smooth surface contour. In some embodiments, the irregular surface contour beads are sold commercially by Bangs Laboratories. In some embodiments, the smooth surface contour beads are Dynal magnetic beads sold commercially by Life Technologies.

Figure 6A:
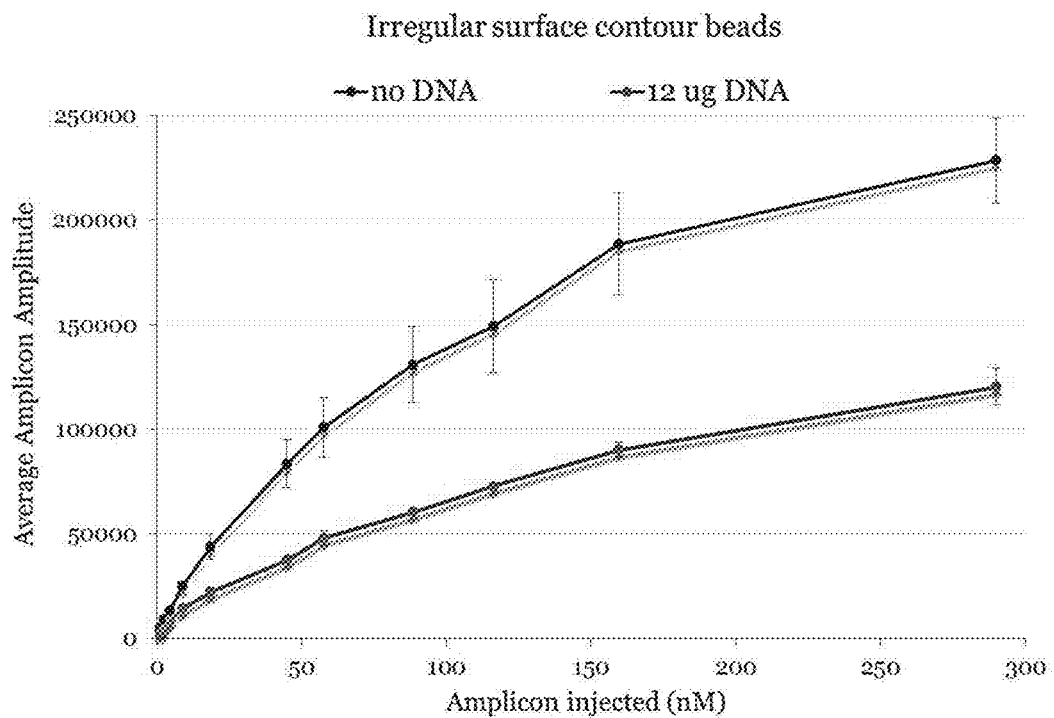
FIG. 6A-6B is a series of plots showing that amine-functionalized beads having a rough surface (e.g., beads comprising surface irregularities that result in micron and sub-micron sized pores) provide for an improved enrichment of samples for small nucleic acids relative to amine-functionalized beads having a relatively smooth surface.
Figure 6B:
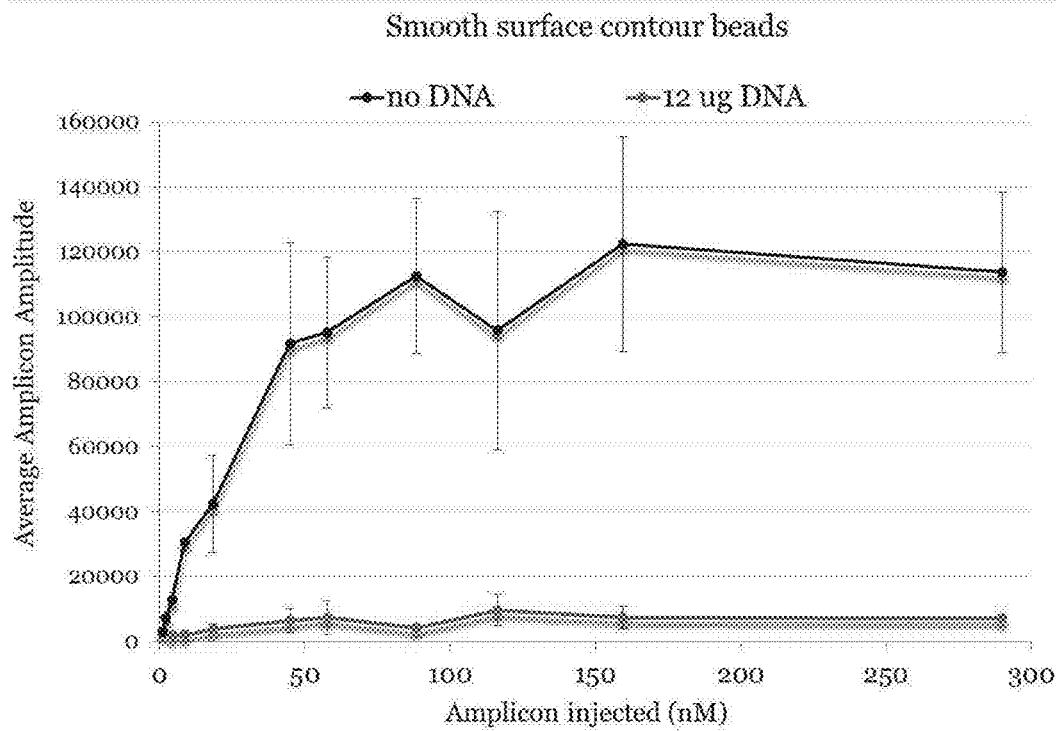

In these experiments, nanomolar concentrations (e.g., from 1 to 300 nanomolar) of a small nucleic acid (e.g., a 150-bp amplicon DNA) were isolated using the amine-functionalized irregular surface and amine-functionalized smooth surface beads in the presence and absence of 12 μg of human genomic DNA. The resulting samples were analyzed by electrospray ionization mass spectrometry (ESI-MS) (see FIG. 6A and FIG. 6B; note different y-axis scales). As shown in FIG. 6A, the small nucleic acid detected by ESI-MS (average amplicon amplitude) after enrichment by irregular surface beads increased as a function of the concentration of small nucleic acid present in the sample prior to enrichment. This phenomenon was observed both for samples comprising only small nucleic acid and for samples comprising small nucleic acid in the presence of large amounts of non-target background nucleic acid (12 μg of human genomic DNA). The maximum signal detected (at 300 nM small nucleic acid) was approximately 100,000 in the presence of large amounts of non-target background nucleic acid (12 μg of human genomic DNA) and approximately 200,000-250,000 in the absence of non-target background nucleic acid.

In contrast, the small nucleic acid detected by ESI-MS (average amplicon amplitude) after enrichment by smooth surface beads in the presence of non-target background nucleic acid (12 μg of human genomic DNA) was extremely low and did not increase with increasing concentration of small nucleic acid present in the sample prior to enrichment (e.g., the amplitude was less than 10,000 for all concentration of small nucleic acid tested in the presence of non-target background nucleic acid). Furthermore, the small nucleic acid detected by ESI-MS (average amplicon amplitude) after enrichment by smooth surface beads in the absence of non-target background nucleic acid reached a maximum value (approximately 100,000-120,000) that was approximately half of the value detected for the irregular surface beads (e.g., compare FIG. 6A and FIG. 6B). Accordingly, the data collected indicated that beads having a rough surface (e.g., beads comprising surface irregularities that result in micron and sub-micron sized pores) provide for an improved enrichment of samples for small nucleic acids relative to beads having a relatively smooth surface.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A method for producing an output sample comprising an increased concentration of small nucleic acids relative to an input sample, the method comprising:
   a) providing an input sample comprising nucleic acids;
   b) incubating said input sample with a carboxylated paramagnetic bead and PEG to produce a bound fraction comprising large nucleic acids and a supernatant fraction comprising small nucleic acids; and
   c) removing said supernatant fraction thereby producing an output sample comprising small nucleic acids.

2. The method of claim 1 wherein said PEG is PEG 8000.

3. The method of claim 2 wherein said PEG 8000 has a concentration of 4% to 5% weight per volume.

4. The method of claim 2 wherein said PEG 8000 has a concentration of approximately 4.8% and said output sample comprises small nucleic acids having a size that is less than or equal to approximately 1000 bp, bases, or nt.

5. The method of claim 2 wherein said PEG 8000 has a concentration of approximately 5.1% and said output sample comprises small nucleic acids having a size that is less than or equal to approximately 600 bp, bases, or nt.

6. The method of claim 1 wherein said small nucleic acids have a length less than a length cutoff value selected from the group consisting of 1000, 900, 800, 700, 600, 500, 400, 300, 275, 250, 225, 200, 175, 150, 125, 100, 75, and 50 base pairs, bases, or nucleotides.

7. The method of claim 6 wherein the distribution of nucleic acid sizes smaller than said length cutoff value in said output sample and distribution of nucleic acid sizes smaller than said length cutoff value in said input sample are the same.

8. The method of claim 1 further comprising d) testing said small nucleic acids in said output sample.

9. The method of claim 8 wherein said testing said nucleic acids comprises testing for a genetic abnormality, a chromosomal aberration, or an aneuploidy; testing for a biomarker associated with a cancer or a neoplastic state; or testing for nucleic acids associated with an infectious agent.

10. The method of claim 8 wherein said testing comprises use of nucleic acid amplification, digital counting by sequencing, hybridization, staining, or mass spectrometry.

11. The method of claim 8 wherein said testing comprises determining a fractional increase or decrease of fetal nucleic acids compared to a control value for a normal fetus.

12. The method of claim 1 wherein said nucleic acids comprise fetal DNA and said input sample is from a pregnant woman.

13. An output sample enriched for small nucleic acids produced by a method according to claim 1.

14. The output sample of claim 13 wherein the ratio of the amount of small nucleic acids in said output sample relative to the amount of small nucleic acids in said input sample is more than 2 to more than 100 or wherein more than 5% to 20% of said nucleic acids in said output sample are small nucleic acids.

15. The method of claim 1 wherein said producing said output sample comprising small nucleic acids further uses one or more of: a) eluting or washing small nucleic acids preferentially from silica; b) retaining large nucleic acids preferentially on silica; c) enriching small nucleic acids by methylated DNA immunoprecipitation with an antibody-coated solid support; d) enriching small nucleic acids by size exclusion; e) enriching small nucleic acids by coefficient of drag alteration sizing; f) enriching small nucleic acids by electrophoresis-based sizing; or g) enriching small nucleic acids by affinity chromatography.

16. The method of claim 15 wherein said affinity chromatography comprises microparticles comprising surface irregularities.

17. The method of claim 15 wherein said eluting or washing said small nucleic acids preferentially from silica comprises washing said small nucleic acids from a silica membrane or column by washing in an ethanol buffer or washing in a buffer comprising TWEEN-20, ethanol, and $MgCl_2$ to produce an output sample in said buffer comprising a higher concentration of small nucleic acids than the concentration of small nucleic acids in the input sample.

18. The method of claim 17, wherein said washing in said buffer comprises 10% TWEEN-20, 15% ethanol, and 20 mM $MgCl_2$ at a ratio of approximately 0.4 to 0.5 buffer volume to sample volume.

19. The method of claim 17, wherein said washing in said ethanol buffer is washing at a wash buffer to sample volume ratio of 0.4 to 1, or said washing in said buffer comprising TWEEN-20, ethanol, and $MgCl_2$ is washing at a wash buffer to sample volume ratio of 0.4 to 1.

20. A method for producing an output sample comprising an increased concentration of small nucleic acids relative to an input sample, the method comprising:
 a) providing an input sample comprising nucleic acids;
 b) incubating said input sample with a carboxylated paramagnetic bead and PEG to produce a bound fraction comprising large nucleic acids and a supernatant fraction comprising small nucleic acids; and
 c) removing said supernatant fraction thereby producing an output sample comprising small nucleic acids wherein said producing said output sample comprising small nucleic acids further uses one or more of: 1) eluting or washing small nucleic acids preferentially from silica wherein said eluting or washing said small nucleic acids preferentially from silica comprises washing said small nucleic acids from a silica membrane or column by washing in an ethanol buffer or washing in a buffer comprising TWEEN-20, ethanol, and $MgCl_2$; 2) retaining large nucleic acids preferentially on silica; 3) enriching small nucleic acids by methylated DNA immunoprecipitation with an antibody-coated solid support; 4) enriching small nucleic acids by size exclusion; 5) enriching small nucleic acids by coefficient of drag alteration sizing; 6) enriching small nucleic acids by electrophoresis-based sizing; or 7) enriching small nucleic acids by affinity chromatography.

21. The method of claim 20, wherein said washing in said buffer comprises 10% TWEEN-20, 15% ethanol, and 20 mM $MgCl_2$ at a ratio of approximately 0.4 to 0.5 buffer volume to sample volume.

22. The method of claim 20, wherein said washing in said ethanol buffer is washing at a wash buffer to sample volume ratio of 0.4 to 1, or said washing in said buffer comprising TWEEN-20, ethanol, and $MgCl_2$ is washing at a wash buffer to sample volume ratio of 0.4 to 1.

* * * * *